(12) United States Patent
Niyaz et al.

(10) Patent No.: US 8,067,588 B2
(45) Date of Patent: Nov. 29, 2011

(54) INSECTICIDAL (1,3,5)-TRIAZINYL PHENYL HYDRAZONES

(75) Inventors: Noormohamed M. Niyaz, Indianapolis, IN (US); Katherine A. Guenthenspberger, Daleville, IN (US); Ricky Hunter, Westfield, IN (US); Annette V. Brown, Indianapolis, IN (US); Jaime S. Nugent, Brownsburg, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 488 days.

(21) Appl. No.: 12/238,954

(22) Filed: Sep. 26, 2008

(65) Prior Publication Data
US 2009/0093481 A1    Apr. 9, 2009

Related U.S. Application Data

(60) Provisional application No. 60/998,204, filed on Oct. 9, 2007.

(51) Int. Cl.
*C07D 251/52* (2006.01)
*C07D 251/54* (2006.01)
*C07D 401/12* (2006.01)
*C07D 403/04* (2006.01)
*A01N 43/68* (2006.01)

(52) U.S. Cl. ........ 544/197; 544/208; 544/113; 514/245; 504/232

(58) Field of Classification Search .................. 544/197, 544/208; 514/245
See application file for complete search history.

(56) References Cited

U.S. PATENT DOCUMENTS

| 6,660,733 | B2 | 12/2003 | Sun et al. |
| 6,693,097 | B2 | 2/2004 | Ono et al. |

FOREIGN PATENT DOCUMENTS

| WO | WO-03030909 | 4/2003 |
| WO | WO-03091223 | 11/2003 |
| WO | WO-2004006867 | 1/2004 |
| WO | PCT/US2008/077875 | 4/2009 |

*Primary Examiner* — Venkataraman Balasubramanian
(74) *Attorney, Agent, or Firm* — Carl D. Corvin; Craig E. Mixan

(57) ABSTRACT

(1,3,5)-Triazinyl phenyl hydrazones are effective at controlling insects.

9 Claims, No Drawings

INSECTICIDAL (1,3,5)-TRIAZINYL PHENYL HYDRAZONES

This application claims the benefit of U.S. Provisional Application Ser. No. 60/998,204 filed on Oct. 9, 2007.

BACKGROUND OF THE INVENTION

The present invention concerns novel (1,3,5)-triazinyl phenyl hydrazones and their use in controlling insects, particularly lepidoptera and/or coleoptera. This invention also includes new synthetic procedures, intermediates for preparing the compounds, pesticide compositions containing the compounds, and methods of controlling insects using the compounds.

There is an acute need for new insecticides and acaricides. Insects and mites are developing resistance to the insecticides and acaricides in current use. At least 400 species of arthropods are resistant to one or more insecticides. The development of resistance to some of the older insecticides, such as DDT, the carbamates, and the organophosphates, is well known. But resistance has even developed to some of the newer pyrethroid insecticides and acaricides. Therefore a need exists for new insecticides and acaricides, and particularly for compounds that have new or atypical modes of action.

The present invention provides novel compounds with broad-spectrum activity against insects, particularly lepidoptera and/or coleoptera.

SUMMARY OF THE INVENTION

This invention concerns compounds useful for the control of insects, especially useful for the control of lepidoptera and/or coleoptera. More specifically, the invention concerns compounds of the formula (I)

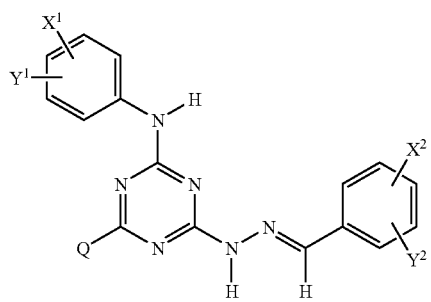

(I)

wherein
$X^1$ and $Y^1$ independently represent H, halogen, CN, $OCH_2CH=CHCl$, $C_1$-$C_6$ haloalkyl, $C_1$-$C_6$ haloalkoxy or $C_1$-$C_6$ halothioalkyl, with the proviso that at least one of $X^1$ or $Y^1$ is not H;
$X^2$ and $Y^2$ independently represent H, halogen, CN, $OCH_2CH=CHCl$, $C_1$-$C_6$ alkoxy, $C_1$-$C_6$ haloalkyl, $C_1$-$C_6$ haloalkoxy or $C_1$-$C_6$ halothioalkyl, with the proviso that at least one of $X^2$ or $Y^2$ is not H;
Q represents H, Cl, $OR^1$ or $NR^2R^3$;
$R^1$ represents $C_1$-$C_4$ alkyl which may be unsubstituted or substituted with from one to the maximum number of chloro or fluoro substituents;
$R^2$ represents H or $C_1$-$C_4$ alkyl;
$R^3$ represents: a) $C_1$-$C_4$ alkyl which may be unsubstituted or substituted with from one to the maximum number of chloro or fluoro substituents, or with a substituent selected from the group consisting of a $C_1$-$C_4$ alkoxy, a $C_1$-$C_4$ alkylamino, a $C_1$-$C_4$ carboalkoxy, a pyridin-3-yl substituted in the 6-position of the pyridine ring with halogen, $C_1$-$C_4$ alkoxy or $C_1$-$C_4$ haloalkyl, a pyrazin-2-yl substituted in the 5-position of the pyrazine ring with ($C_1$-$C_4$)alkyl, and a morpholin-4-yl substituent; or b) $NR^2R^3$ taken together represent:

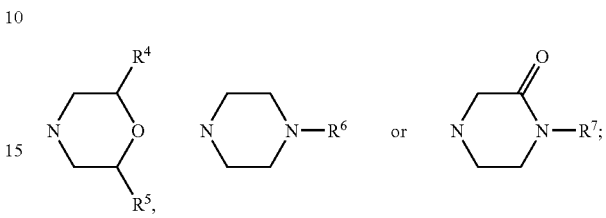

$R^4$, $R^5$ and $R^7$ independently represent H or $CH_3$; and
$R^6$ represents H, $C_1$-$C_4$ alkyl or —$C(O)R^4$;
or a phytologically acceptable acid addition salt thereof.
Preferred compounds of formula (1) include the following classes:
(A) Compounds of formula (1) wherein one of $X^1$ and $Y^1$ are F, Cl, Br, CN, $CF_3$, $OCF_3$ or $OCF_2CHF_2$.
(B) Compounds of class (A) wherein $X^1$ and $Y^1$ are meta- or para-substituents.
(C) Compounds of formula (1) wherein one of $X^2$ and $Y^2$ are F, Cl, Br, CN, $CF_3$, $OCF_3$ or $OCF_2CHF_2$.
(D) Compounds of class (C) wherein $X^2$ and $Y^2$ are meta- or para-substituents.
(E) Compounds of formula (1) wherein Q represents

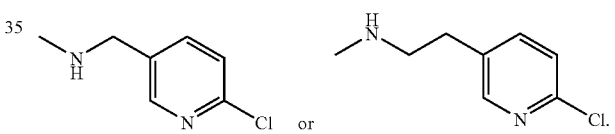

It will be appreciated by those skilled in the art that the most preferred compounds are generally those which are comprised of combinations of the above preferred classes.

The invention also provides new processes and intermediates for preparing compounds of formula (I) as well as new compositions and methods of use, which will be described in detail hereinafter.

DETAILED DESCRIPTION OF THE INVENTION

Throughout this document, all temperatures are given in degrees Celsius, and all percentages are weight percentages unless otherwise stated.

Unless specifically limited otherwise, the term "alkyl", as well as derivative terms such as "alkoxy" and "thioalkyl", as used herein, include within their scope straight chain, branched chain and cyclic moieties.

Unless specifically limited otherwise, the term "halogen", as well as derivative terms such as "halo", as used herein, refers to fluorine, chlorine, bromine, and iodine. Preferred halogens are fluorine and chlorine.

The term "haloalkyl" refers to alkyl groups substituted with from one up to the maximum possible number of halogen atoms. The terms "haloalkoxy" and "halothioalkyl" refer to alkoxy and thioalkyl groups substituted with from one up to the maximum possible number of halogen atoms.

Unless otherwise indicated, when it is stated that a group may be substituted with one or more substituents selected from an identified class, it is intended that the substituents may be independently selected from the class.

Compounds of the formula (I) can be synthesized from commercially available cyanuric chloride (II) by stepwise addition of nucleophiles ("Triazine Antiviral Compounds" Arenas, Jaime, E., Fleming, Elizabeth, S. WO 9936410, "Triazine Antiviral Compounds" Arenas, Jaime, E., Fleming, Elizabeth, S. Xiang, Yi, B. U.S. Pat. No. 6,335,339 B1 and "Inhibitors of IL-12 Production" Ono, Mitsunori, Wada, Yumiko, Brunkhorst, Beatrice, Warchol, Tadeusz, Wrona, Wojciech, Zhou, Dan, Vo, Nha, H. WO 0078757 A1). More particularly, the compounds of the formula (I) can also be synthesized according to the chemical processes outlined in Schemes A-E below.

Commercially available cyanuric chloride (II) can be condensed with one equivalent of an aryl amine of the formula (III) in the presence of a base in a polar aprotic solvent to afford the mono aminated triazine derivative of the formula (IV) (Scheme A). Potassium carbonate is the preferred base for coupling, however, any organic or inorganic base can be used.

Scheme A

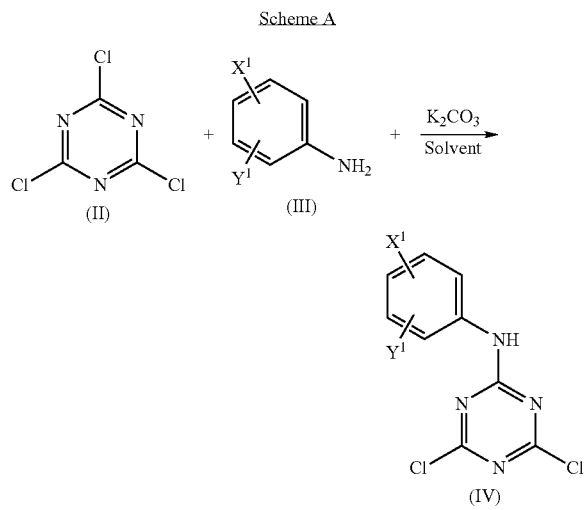

The 2-arylamino-4,6-dichloro-1,3,5-triazine of the formula (IV) can be reacted with one equivalent of a metal alkoxide (MOR$^1$) or amine nucleophile NR$^2$R$^3$ in a polar aprotic solvent to afford the compound of the formula (V) (where R$^1$, R$^2$ and R$^3$ are defined as above) (Scheme B). Sodium hydride is used as the preferred base for generation of the metal alkoxide MOR$^1$ (M=Na), although other bases can also be used. The preferred base and solvent for the reaction of amines NHR$^2$R$^3$ are i-Pr$_2$(Et)N and dioxane, respectively, although other bases and polar aprotic solvents can be used.

Scheme B

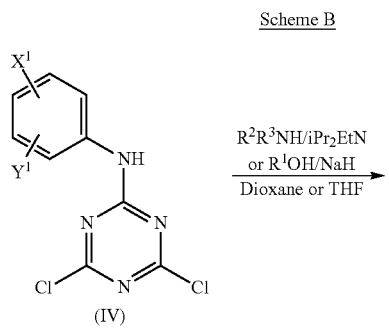

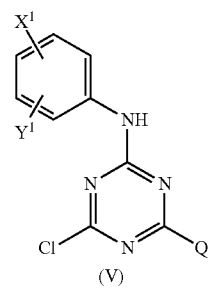

where Q represents —NR$^2$R$^3$ or —OR$^1$.

The triazine derivative of the formula (V) can be reacted with excess hydrazine monohydrate in dioxane to give the corresponding hydrazinotriazine derivative of the formula (VI) (Scheme C). In most cases the product (VI) is purified by a simple filtration and drying under vacuum.

Scheme C

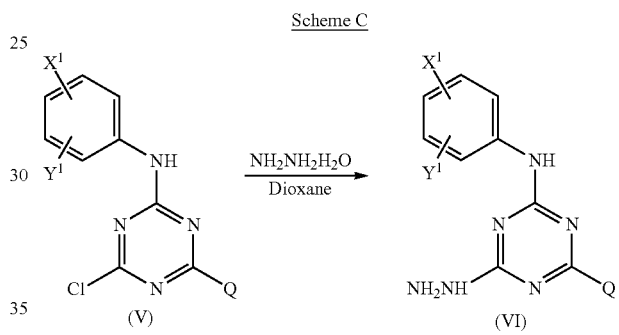

where Q represents Cl, —NR$^2$R$^3$ or —OR$^1$.

Compounds of formula (VII) where Q is Cl can be converted to compounds of formula (VIII) (Scheme D) by catalytic hydrogenolysis using hydrogen in the presense of a catalyst such as palladium on carbon in an organic solvent such as methanol. While catalytic hydrogenolysis is one convenient method for the preparation of compounds of formula (VIII), other methods known to those skilled in the art can also be employed (for examples see: Advanced Organic Chemistry, forth edition, J. March, John Wiley and Sons, 1992). The products can be recovered and purified by conventional methods.

Scheme D

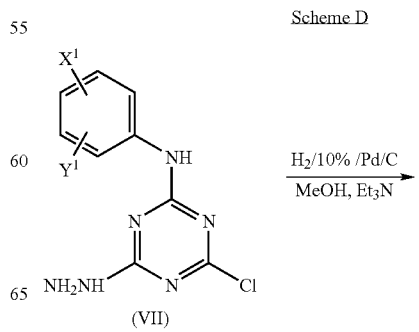

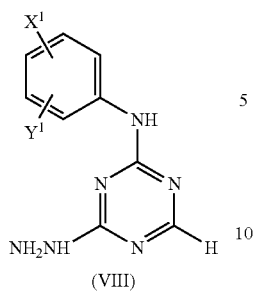

(VIII)

In the last step, the hydrazino 1,3,5-triazine derivative (IX) can be reacted with an aryl aldehyde of the formula (X) in ethanol or a mixture of ethanol and another solvent such as tetrahydrofuran or dichloromethane to give the arylamino-1,3,5-triazinohydrazone of the formula (I) (Scheme E).

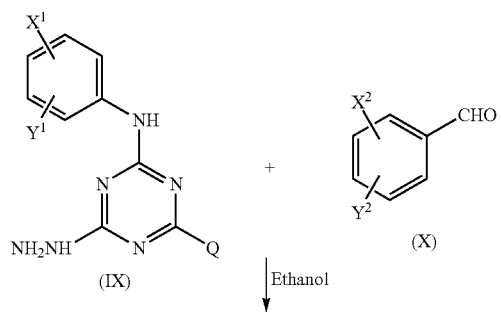

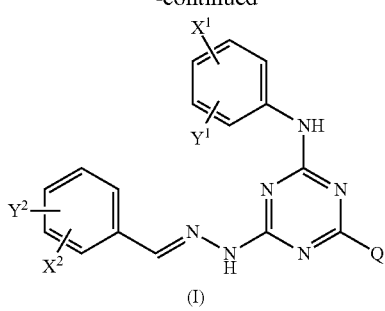

(I)

where Q represents H, Cl —NR$^2$R$^3$ or —OR$^1$.

While Schemes A-E depict a particular sequence, Schemes A and B can conveniently be performed in either order. It is, however, preferable to conduct Schemes C thru E after Schemes A and B have been completed.

Alternatively, compounds of formula (I) can also be prepared by the methods illustrated in Scheme F.

In the first step, 4,6-dichloro-2-arylaminotriazine intermediate of the formula (IV) is treated with the arylhydrazone of the formula (XI) in the presence of a base in an aprotic solvent such as dioxane to afford the compound of the formula (Ia) (Scheme F). i-Pr$_2$(Et)N is the preferred base although any other base can be used. Compound of the formula (Ia) is then reacted with the nucleophile HNR$^2$R$^3$ or HOR$^1$ in the presence of a base in an aprotic solvent to afford compound of the formula (I). The aryl hydrazone of the formula (XI) can be prepared from the corresponding aryl aldehyde (*J. Org. Chem.* 1966, 31, 677).

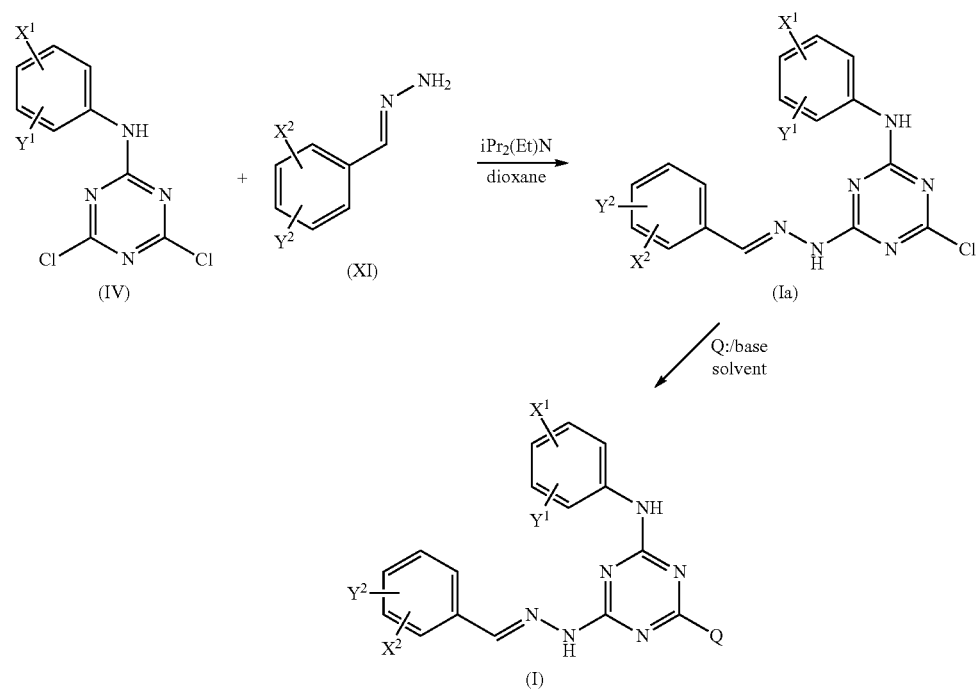

where Q represents —NR$^2$R$^3$ or —OR$^1$.

EXAMPLES

Example 1

Preparation of (4-Morpholin-4-yl-6-{N'-[4-(1,1,2,2-tetrafluoroethoxy)benzylidene]hydrazino}-1,3,5-triazin-2-yl)-(4-triflurormethoxyphenyl)amine (1) (Scheme G)

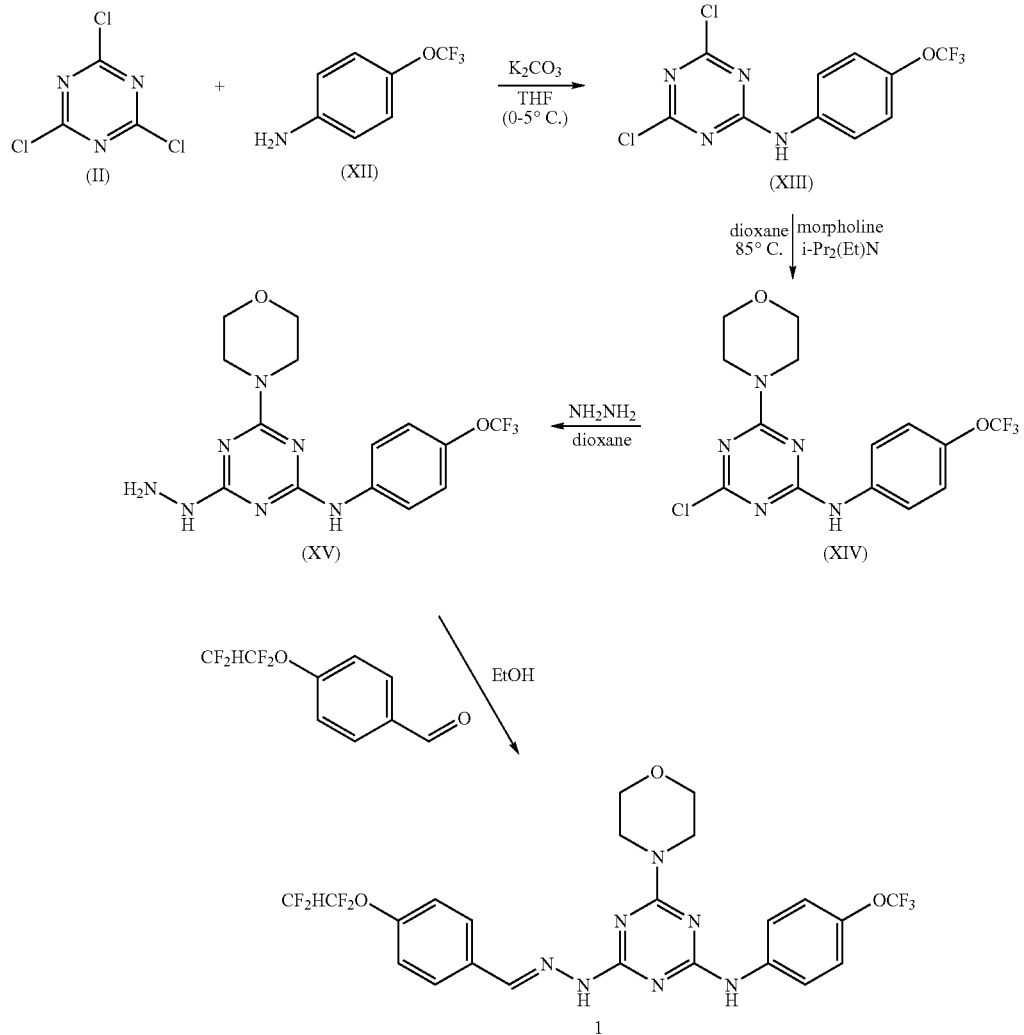

(4,6-Dichloro-1,3,5-triazin-2-yl)-(4-trifluoromethoxyphenyl)amine (XIII)

A solution of 4-trifluoromethoxyaniline (XII) (14.66 mL, 108 mmol) in dry tetrahydrofuran (THF; 120 mL) was added, dropwise, to a cold (0-5° C.) stirred suspension of cyanuric chloride (II) (20.0 g, 108 mmol) and potassium carbonate (15 g, 108 mmol) in dry THF (400 mL). The reaction mixture was stirred for 3 h while slowly warming to ambient temperature. After stirring for 14 h at ambient temperature, the reaction mixture was diluted with ethyl acetate (400 mL) and then acidified with 1 N aqueous hydrochloric acid. The organic phase was separated, rinsed successively with water, saturated aqueous sodium bicarbonate and brine, dried over anhydrous magnesium sulfate, filtered and concentrated under vacuum on a rotary evaporator. The residue, an off white solid, was recrystallized from hot hexanes to afford (4,6-dichloro-1,3,5-triazin-2-yl)-(4-trifluoromethoxyphenyl)amine (XIII) (35.1 g, 99% yield): m.p. 119-122° C.; $^1$H NMR (CDCl$_3$) δ 7.62 (d, J=3.3 Hz, 2H), 7.58 (d, J=2.2 Hz, 2H); ESI/MS 325 (M+H), 323 (M−H); Anal. Calcd. For $C_{10}H_5Cl_2F_3N_4O$: C, 36.95; H, 1.55; N, 17.53. Found: C, 36.80; H, 1.53; N, 16.98.

(4-Chloro-6-morpholin-4-yl-1,3,5-triazin-2-yl)-(4-trifluoromethoxyphenyl)amine (XIV)

To a stirred solution of (4,6-dichloro-1,3,5-triazin-2-yl)-(4-trifluoromethoxyphenyl)amine (XIII) (5.0 g, 15.3 mmol) in dioxane (25 mL) was added i-Pr$_2$(Et)N (2.37 g, 18.3 mmol) and morpholine (1.60 g, 18.3 mmol), and the resulting mixture heated at 85° C. for 12 hours. The reaction mixture was cooled to ambient temperature, diluted with water and stirred for 1 h. The white precipitate was filtered and dried under vacuum to give (4-chloro-6-morpholin-4-yl-1,3,5-triazin-2-yl)-(4-trifluoromethoxyphenyl)amine (XIV) (5.63 g, 98% yield): GC/MS m/z 375 (M+); $^1$H NMR (CDCl$_3$) δ 7.55 (d, J=3.7 Hz, 2H), 7.51 (bs, 1H), 7.25 (d, J=2.2 Hz, 2H), 3.74-3.87 (m, 8H).

(4-Hydrazino-6-morpholin-4-yl-1,3,5-triazin-2-yl)-(4-trifluoromethoxyphenyl)amine (XV)

To a solution of (4-chloro-6-morpholin-4-yl-1,3,5-triazin-2-yl)-(4-trifluoromethoxyphenyl)amine (XIV) (3.0 g, 8.51 mmol) in dioxane (16 mL) was added hydrazine hydrate (2 mL) and the mixture stirred at ambient temperature for 30 min. The mixture was diluted with water and the resulting slurry stirred for 10 min and filtered under vacuum. The white precipitate was washed with copious amount of water and dried under vacuum to give (4-hydrazino-6-morpholin-4-yl-1,3,5-triazin-2-yl)-(4-trifluoromethoxyphenyl)amine (XV) (3.01 g, 95% yield): $^1$H NMR (CDCl$_3$) δ 7.55 (d, J=8.4 Hz, 2H), 7.13 (d, J=8.4 Hz, 2H), 3.74-3.87 (m, 8H); ESI/MS 372 (M+H), 370 (M−H).

(4-Morpholin-4-yl-6-{N'-[4-(1,1,2,2-tetrafluoroethoxy)benzylidene]hydrazino}-1,3,5-triazin-2-yl)-(4-trifluoromethoxyphenyl)amine (1)

A 10 mL flask was charged with (4-hydrazino-6-morpholin-4-yl-1,3,5-triazin-2-yl)-(4-trifluoromethoxyphenyl)amine (XV) (159 mg, 0.43 mmol), 4-(1,1,2,2-tetrafluoroethoxy)benzaldehyde (142 μL, 0.86 mmol), and ethanol (5 mL) and the mixture was stirred at ambient temperature for 24 h. Water (5 mL) was added to the reaction mixture which was then extracted with EtOAc (3×5 mL). The combined organic extract was washed with brine (10 mL), dried over sodium sulfate, filtered, and concentrated under vacuum. Flash chromatography (silica gel, 10% EtOAc/cyclohexane) afforded compound 1 (167 mg, 68% yield): m.p. 203-206° C.; $^1$H NMR (CDCl$_3$) δ 8.65 (s, 1H), 7.79 (s, 1H), 7.66-7.55 (m, 4H), 7.20-7.12 (m, 4H), 6.10-5.73 (tt, J$_1$=53.1 Hz, J$_2$=2.56 Hz, 1H), 3.86-3.75 (m, 8H).

Example 2

Preparation of N-(6-Chloropyridin-3-ylmethyl)-N'-(4-fluoro-3-trifluoromethyl-phenyl)-6-{N'-[1-(4-trifluoromethoxyphenyl)-methylidene]-hydrazino}-[1,3,5]triazine-2,4-diamine (2) (Scheme H)

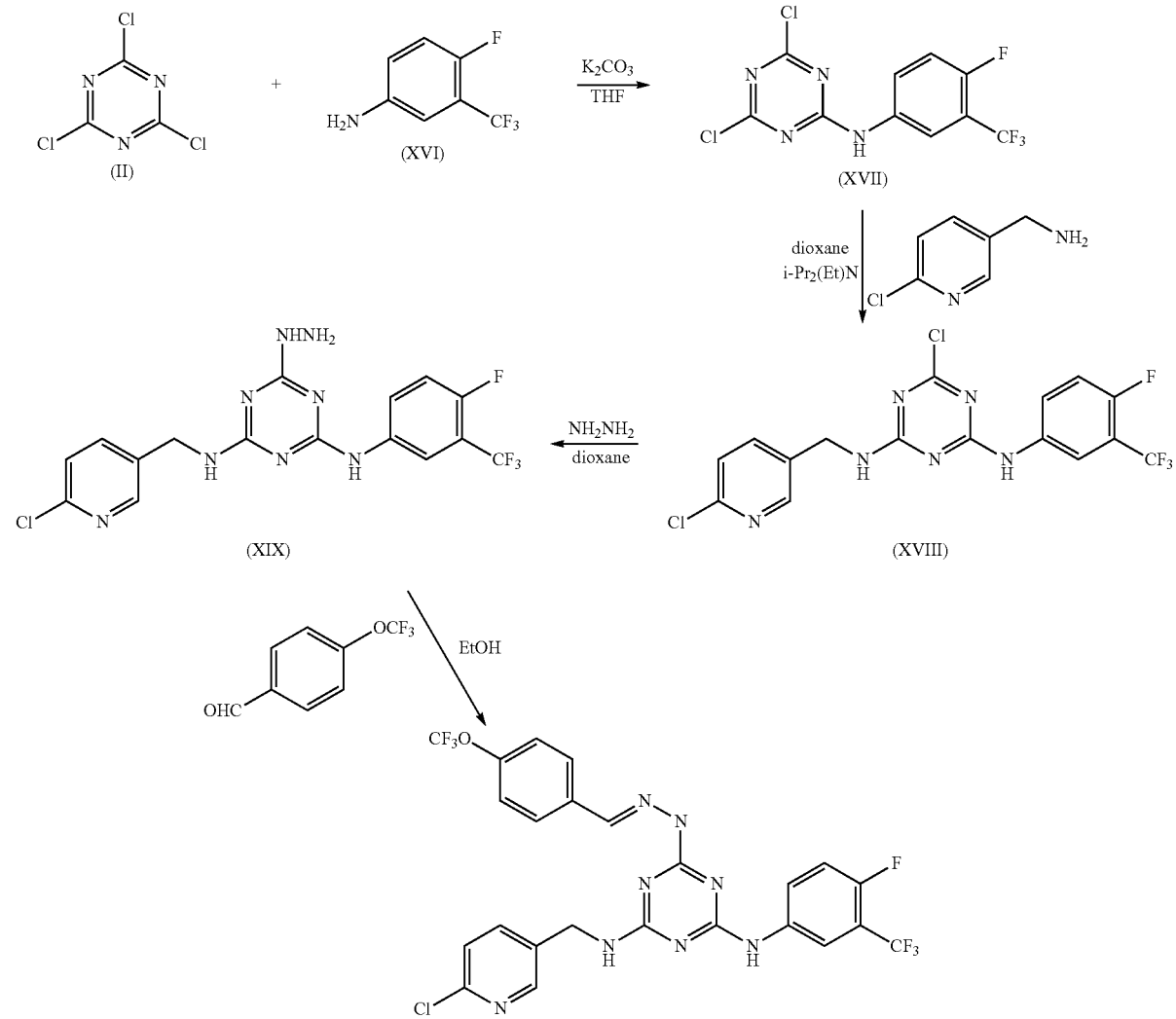

2

(4,6-Dichloro-[1,3,5]triazin-2-yl)-(4-fluoro-3-trifluoromethylphenyl)amine (XVII)

Potassium carbonate (2.76 g, 20 mmol) was added to a solution of cyanuric chloride (II) (1.84 g, 10 mmol) in THF (30 mL) and the mixture cooled to 0-5° C. in an ice bath. 3-Trifluoromethyl-4-fluoroaniline (XVI) (1.79 g, 10 mmol) was added dropwise with stirring. The mixture was stirred for 16 h, diluted with water (50 mL) and extracted with ethyl acetate (3×20 mL). The combined organic extract was rinsed with brine (20 mL), dried over magnesium sulfate and concentrated under vacuum. The residue was purified by chromatography (silica gel; EtOAc/hexane (1:4)) to afford 4,6-dichloro-N-(3-trifluoromethyl-4-fluorophenyl)-1,3,5-triazine-2-amine (XVII) as an off-white solid (0.9 g, 19% yield): m.p. 114-117° C.; $^1$H NMR (CDCl$_3$) δ 7.80 (s, 1H), 7.86 (m, 2H), 7.65 (bs, 1H), 7.27 (t, 1H); ESI/MS 326 (M+H).

6-Chloro-N-(6-chloropyridin-3-ylmethyl)-N'-(4-fluoro-3-trifluoromethylphenyl)-1,3,5-triazine-2,4-diamine (XVIII)

To a stirred solution of (4,6-Dichloro-[1,3,5]triazin-2-yl)-(4-fluoro-3-trifluoromethylphenyl)amine (XVII) (2.0 g, 6.11 mmol) in dioxane (5 mL) was added i-Pr$_2$(Et)N (0.832 g, 6.44 mmol) and (6-chloropyridin-3-yl)methylamine (0.912 g, 6.44 mmol), and the mixture heated at 50° C. for 12 h. The mixture was cooled to ambient temperature and diluted with water and ethyl acetate. The organic phase was separated, washed with brine and concentrated under vacuum to give 1 6-chloro-N-(6-chloropyridin-3-ylmethyl)-N'-(4-fluoro-3-trifluoromethylphenyl)-1,3,5-triazine-2,4-diamine (XVIII) (1.60 g (60% yield): $^1$H NMR (DMSO) δ 8.32 (bs, 1H), 7.98 (bs, 1H), 7.58 (bd, 1H), 7.28 (m, 3H), 7.16 (t, J=9.0 Hz, 1H), 6.60 (bs, 1H), 4.64 (m, 2H); ESI/MS 433 (M+H), 431 (M−H).

N-(6-Chloro-pyridin-3-ylmethyl)-N'-(4-fluoro-3-trifluoromethylphenyl)-6-hydrazino-[1,3,5]triazine-2,4-diamine (XIX)

To a solution of 6-Chloro-N-(6-chloropyridin-3-ylmethyl)-N'-(4-fluoro-3-trifluoromethylphenyl)-[1,3,5]triazine-2,4-diamine (XVIII) (3.0 g, 6.9 mmol) in dioxane (30 mL) was added hydrazine hydrate (2 mL), and the mixture stirred at ambient temperature for 30 min. The mixture was diluted with water, the resulting slurry stirred for 10 min and filtered under vacuum to give a white solid. This solid was washed with water and dried under vacuum to give N-(6-chloropyridin-3-ylmethyl)-N'-(4-fluoro-3-trifluoromethylphenyl)-6-hydrazino-1,3,5-triazine-2,4-diamine(XIX) (2.89 g, 97% yield): $^1$H NMR (CDCl$_3$); δ 9.40 (m, 1H), 8.5-7.5 (m, 4H), 7.45 (m, 2H), 7.33 (m, 2H), 4.49, m, 2H), 4.17 (bs, 2H); ESI/MS 429 (M+H), 427 (M−H).

Preparation of N-(6-Chloropyridin-3-ylmethyl)-N'-(4-fluoro-3-trifluoromethyl-phenyl)-6-{N'-[1-(4-trifluoromethoxyphenyl)-methylidene]-hydrazino}-[1,3,5]triazine-2,4-diamine (2)

A 20 mL flask was charged with N-(6-chloropyridin-3-ylmethyl)-N'-(4-fluoro-3-trifluoromethylphenyl)-6-hydrazino-1,3,5-triazine-2,4-diamine (XIX) (285 mg, 0.66 mmol), 4-(trifluoromethoxy)benzaldehyde (251 mg, 1.32 mmol), and ethanol (10 mL), and the resulting mixture stirred at ambient temperature for 24 h. The mixture was concentrated under vacuum, the residue washed with hexanes and recrystallized from hexanes-ethyl ether to afford the titled compound (2) as a white solid (182 mg, 45% yield): m.p. 117-125° C.; $^1$H NMR (CDCl$_3$): δ 8.65 (bs, 1H); 8.54 (d, J=4.5 Hz, 1H); 8.35 (bs, 1H); 7.84 (s, 1H); 7.73 (d, J=7.2 Hz, 2H); 7.49-7.7 (m, 4H); 7.26 (m, 3H); 7.2 (t, J=6.0 Hz, 1H); 4.66 (d, J=6.0 Hz, 2H); Anal. Calcd for C$_{24}$H$_{17}$F$_7$N$_8$O: C, 50.89, H, 3.03, N, 19.78. Found C, 50.49; H, 3.17; N, 19.31

Alternative Preparation of N-(6-Chloro-pyridin-3-ylmethyl)-N'-(4-fluoro-3-trifluoromethyl-phenyl)-6-{N'-[1-(4-trifluoromethoxyphenyl)-methylidene]-hydrazino}-[1,3,5]triazine-2,4-diamine (2) (Scheme I)

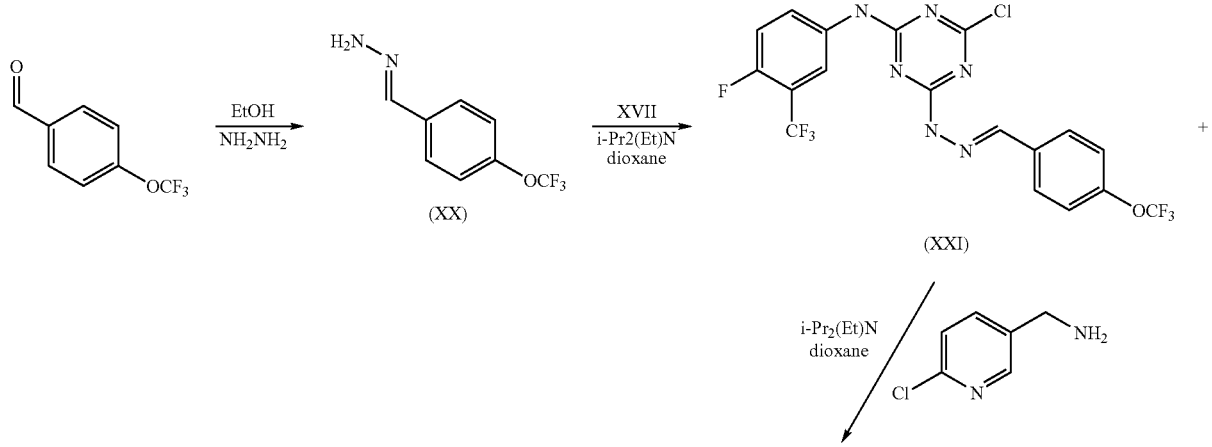

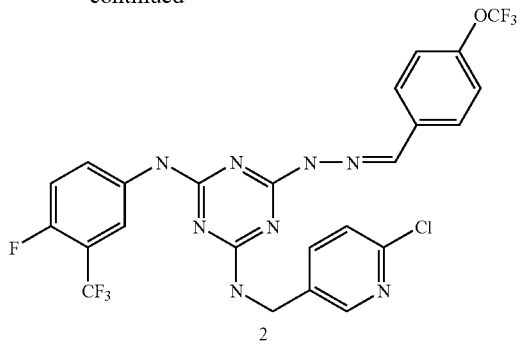

[1-(4-Trifluoromethoxyphenyl)-methylidene]-hydrazine (XX)

Hydrazine (3.3 mL, 105 mmol) was dissolved in ethanol (10 mL) at room temperature. To this solution was added 4-trifluoromethoxybenzaldehyde (5.0 mL, 35 mmol) dropwise over 25 min. The reaction mixture was stirred an additional 45 min and concentrated under vacuum. The residue was dissolved in ethyl ether (20 mL) and washed with water (10 mL). The water layers were extracted with ethyl ether (3×15 mL), and the combined organic layer was dried over magnesium sulfate, filtered and concentrated to give [4-(trifluoromethoxy)benzylidene]hydrazine (XX) as a yellow oil (6.5 g, 91% yield). $^1$H NMR (DMSO-$d_6$): δ 7.69 (s, 1H); δ 7.56 (d, J=8.7 Hz, 2H) δ 7.30 (d, J=7.8 Hz, 2H); δ 6.94 (bs, 2H); GC-MS m/z 204 (M+).

(4-Chloro-6-{N'-[1-(4-trifluoromethoxyphenyl)-methylidene]-hydrazino}-[1,3,5]triazin-2-yl)-(4-fluoro-3-trifluoromethylphenyl)-amine (XXI)

4,6-Dichloro-N-(3-trifluoromethyl-4-fluorophenyl)-1,3,5-triazine-2-amine (XVII) (2.0 g, 6.2 mmol) was dissolved in dioxane (40 mL). Diisopropylethylamine (1.6 mL, 9.32 mmol) was added followed by [4-(trifluoromethoxy)benzylidene]hydrazine (XX) (1.3 g, 6.2 mmol). The reaction was stirred at room temperature overnight. The solvent was removed under vacuum, and the residue diluted with ethyl ether (25 mL). The organic phase was washed with brine, dried over magnesium sulfate, filtered and concentrated to a yellow powder. This powder was washed with acetonitrile to give {4-chloro-6-[N'-(4-trifluoromethoxybenzylidene)hydrazino]-1,3,5-triazin-2-yl}-(4-fluoro-3-trifluoromethylphenyl)-amine (XXI) as a white solid; (2.1 g, 67% yield): m.p. 109-111° C.; $^1$H NMR (CDCl$_3$): δ 8.9, (bs, 1H); 8.5 (bs, 1H); 7.95 (s, 1H); 7.75 (bs, 2H); 7.45 (bs, 1H); 7.24 (m, 4H); ESI/MS 494 (M+H).

N-(6-Chloropyridin-3-ylmethyl)-N'-(4-fluoro-3-trifluoromethylphenyl)-6-{N'-[1-(4-trifluoromethoxyphenyl)-methylidene]-hydrazino}-[1,3,5]triazine-2,4-diamine (2)

{4-Chloro-6-[N'-(4-trifluoromethoxybenzylidene)hydrazino]-1,3,5-triazin-2-yl}-(4-fluoro-3-trifluoromethylphenyl)amine (XXI) (2.54 g, 5.14 mmol) was dissolved in dioxane (25 mL). To this solution was added diisopropylethylamine (1.8 mL, 10.3 mL) followed by 3-aminomethyl-6-chloropyridine (0.52 mL, 5.17 mmol). The reaction was allowed to stir overnight at room temperature. The solvent was removed under vacuum and the residue dissolved in ethyl ether (40 mL). This solution was rinsed with brine, dried over magnesium sulfate, filtered and concentrated to give a dark yellow oil which was purified by column chromatography (silica, gel, hexane/EtOAc), to afford desired product 2 (0.93 g, 32% yield).

Example 3

Preparation of (4-Fluoro-3-trifluoromethyl-phenyl)-(4-{N'-[1-(4trifluoromethoxy-phenyl)-methylidene]-hydrazino}-[1,3,5]triazin-2-yl)-amine (3) (Scheme J)

Scheme J

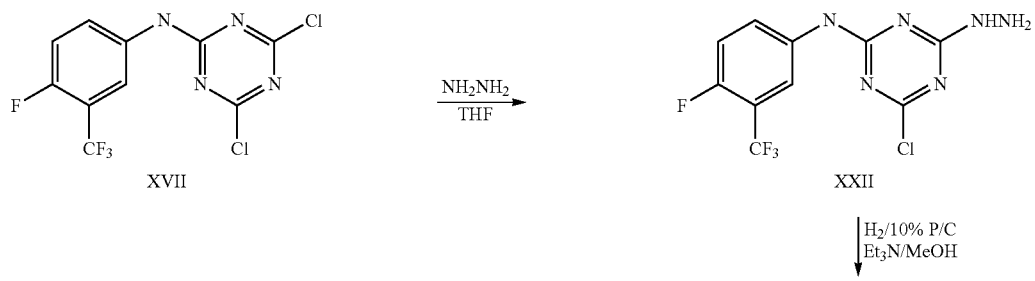

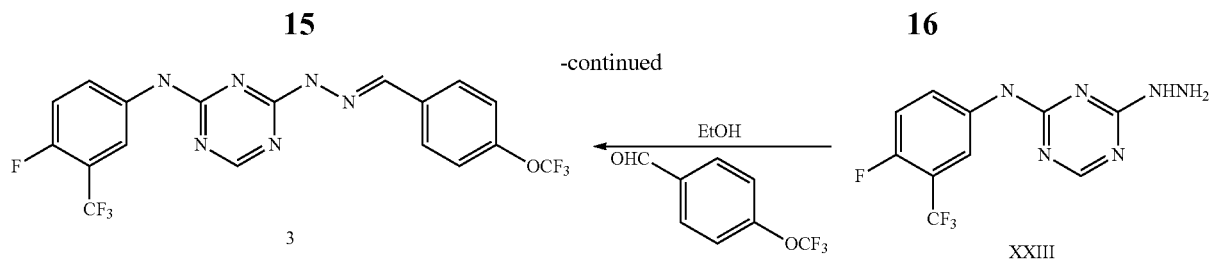

(4-Chloro-6-hydrazino-[1,3,5]triazin-2-yl)-(4-fluoro-3-trifluoromethyl-phenyl)-amine (XXII)

To a solution of the compound XVII (1.83 g, 6 mmol) in THF (10 mL) was added hydrazine monohydrate (0.84 mg, 17 mmol) and the mixture was stirred at room temperature over night. The mixture was concentrated to a volume of about 3 mL and diluted with ethyl acetate (50 mL) and water (10 mL). The organic phase was separated, rinsed with brine, dried over anhydrous magnesium sulfate, filtered and the solvent removed in vacuo to afford the titled compound XXII (1.5 g, 83% yield, 92% purity): ESI/MS 319 (M+H), 317(M−H); $^1$H NMR (DMSO-$d_6$): δ 10.40 (bs, 1H), 9.24 (bs, 1H), 8.08 (m, 1H), 7.42 (m, 2H), 4.43 (m, 2H)

(4-Fluoro-3-trifluoromethylphenyl)-(4-hydrazino-[1,3,5]triazin-2-yl)-amine (XXIII)

A mixture of compound XXII (1.5 g, 0.005 mol), triethylamine (1.41 g, 0.014 mol) and palladium on carbon (10% w/w) (0.45 g) in methanol (100 mL) was purged with nitrogen, and then shaken in a Par apparatus under an atmosphere of hydrogen gas (45 psi pressure) for 3 days. The mixture was purged with nitrogen, concentrated in vacuo to a volume of ca. 20 mL, diluted with water (50 mL) and ethyl acetate (100 mL). The biphasic mixture was filtered to remove the catalyst and the organic phase separated, rinsed with brine, dried over anhydrous magnesium sulfate, and concentrated in vacuo to afford the titled compound XXIII as a white solid (0.64 g, 48% yield, crude): m.p. 181-182° C.; ESI/MS 289 (M+H) 287 (M−H).

(4-Fluoro-3-trifluoromethylphenyl)-(4-{N'-[1-(4-trifluoromethoxyphenyl)-methylidene]-hydrazino}-[1,3,5]triazin-2-yl)-amine (3)

To a solution of (4-Chloro-6-hydrazino-[1,3,5]triazin-2-yl)-(4-fluoro-3-trifluoromethylphenyl)-amine(XXIII) (264 mg, 1.38 mmol) in ethanol (8 mL) was added trifluoromethoxybenzaldehyde (200 mg, 0.694 mmol). The mixture was stirred overnight and filtered to give a white precipitate. The mother liquor was concentrated in vacuo and the residue recrystallized from ethyl acetate. The solids were combined and dried in vacuo to afford the titled compound 3 as white solid (123 mg, 38% yield): m.p. 185-186° C.; ESI/MS 461 (M+H), 459(M−H); $^1$H NMR (CDCl$_3$): δ 8.5 (bs, 1H), 7.95 (s, 1H), 7.80 (m, 2H), 7.65 (m, 1H), 7.2-7.4, m, 6H).

Example 4

Insecticidal Testing

The compounds identified in Table 1 were prepared according to the previous methods and were tested against beet armyworm and corn earworm as follows:
Insecticidal Test for Corn Earworm (*Helicoverpa Zea*) and Beet Armyworm (*Spodoptera Exigua*).

To prepare test solution, the test compound was formulated at 2000 ppm solution as 4 mg/2 mL of 9 acetone: 1 tap water. 50 μL of the 2000 ppm (equivalent to 50 μg/cm$^2$ dose on diet surface area) test solution was pipetted upon the surface of 1 mL of lepidopteran diet (Southland Multi-Species Lepidopteran Diet) contained in each of eight wells per insect species (one well=1 replication). A second-instar corn earworm and beet armyworm was placed upon the treated diet in each well once the solvent had air-dried. Trays containing the treated diet and larvae were covered and then held in a growth chamber at 25° C., 50-55% RH, and 16 hr light:8 hr dark for 5 days. Observation were conducted 5 days after treatment and infestation. The number of dead insects of 8 per species per treatment was then determined and the results are given in Table 1 as a percent control at a dose of 50 mg/cm$^2$.

Keys to the table: Mass spectral data were obtained using liquid chromatography mass spectroscopy (LC-MS). The masses are detected using electrospray ionization (ESI) and reported as Mol Ion (M+H, M−H); AVG LAPHEG 50 refers to activity against beet army worm (*Spodoptera exigua*) as defined above; AVG HELIZE 50 refers to activity against corn ear worm (*Helicoverpa zea*) as described above.

TABLE 1

| Cmpd# | Molecular Structure | Mol Ion (M + H, M − H) | Phys. APP | AVG LAPHEG 50 | AVG HELIZE 50 |
|---|---|---|---|---|---|
| 1 | 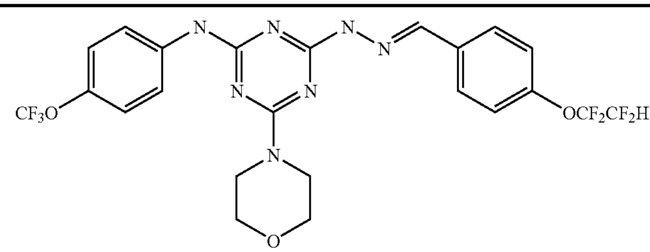 | 576, 574 | white solid | 100 | 100 |

TABLE 1-continued

| # | Structure | MS | Appearance | | |
|---|---|---|---|---|---|
| 2 | 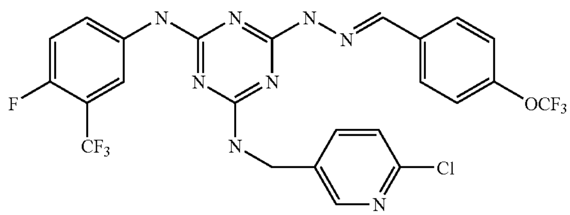 | 601, 599 | white solid | 100 | 100 |
| 3 | 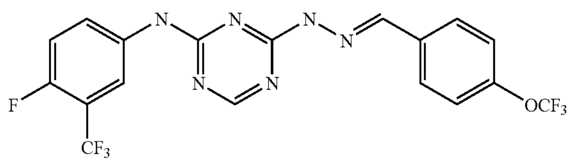 | 459, 461 | white solid | 100 | 100 |
| 4 | 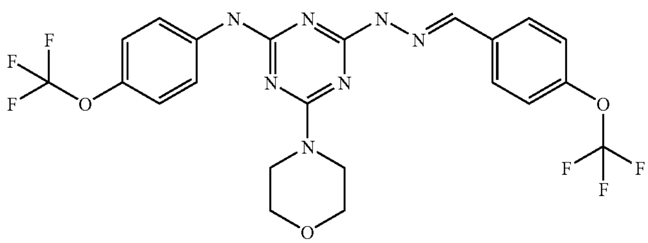 | 544, 542 | white solid | 100 | 100 |
| 5 | 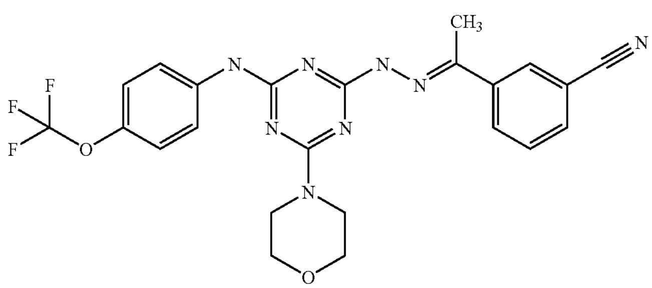 | 500, 498 | white solid | 100 | 100 |
| 6 | 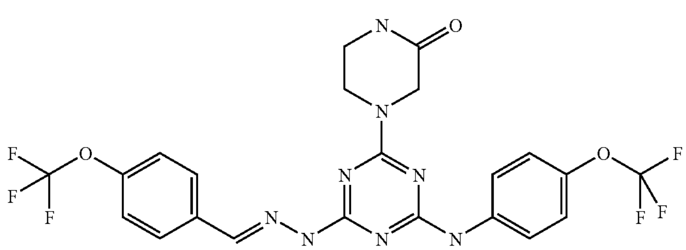 | 557, 555 | white solid | 100 | 100 |
| 7 | 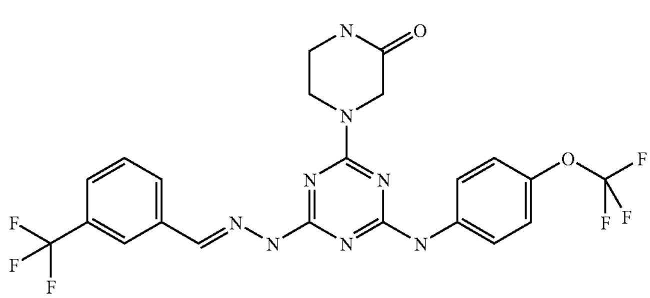 | 541, 539 | white solid | 100 | 100 |

TABLE 1-continued

| # | Structure | Mass | Appearance | | |
|---|---|---|---|---|---|
| 8 | (structure) | 503, 501 | off white solid | 25 | 25 |
| 9 | (structure) | 503, 501 | off white solid | 25 | 25 |
| 10 | (structure) | 487, 485 | off white solid | 13 | 0 |
| 11 | (structure) | 437, 435 | off white solid | 13 | 100 |
| 12 | (structure) | 487, 485 | off white solid | 100 | 100 |
| 13 | (structure) | 471, 469 | clear yellow oil | 0 | 75 |
| 14 | (structure) | 433, 431 | yellow glass | 25 | 13 |

| # | Structure | Mass | Appearance | | |
|---|---|---|---|---|---|
| 15 | (structure: bis(4-trifluoromethoxyphenyl) triazine with 2-methoxyethylamino group) | 532, 530 | off white solid | 100 | 88 |
| 16 | (structure: bis(4-trifluoromethoxyphenyl) triazine with ethylamino group) | 502, 500 | off white solid | 13 | 0 |
| 17 | (structure: 4-fluorophenyl / 4-trifluoromethoxyphenyl triazine with 2-methoxyethylamino group) | 466, 464 | off white solid | 50 | 63 |
| 18 | (structure: 4-fluorophenyl / 4-trifluoromethoxyphenyl triazine with ethylamino group) | 436, 434 | off white solid | 75 | 38 |
| 19 | (structure: 4-trifluoromethoxyphenyl / 3-trifluoromethylphenyl triazine with 2-methoxyethylamino group) | 516, 514 | off white solid | 100 | 75 |
| 20 | (structure: 4-fluorophenyl / 3-trifluoromethylphenyl triazine with 2,2,2-trifluoroethylamino group) | (no M + 1), 488 | off white solid | 13 | 50 |

TABLE 1-continued

| | | | | | |
|---|---|---|---|---|---|
| 21 | [structure] | 587, 585 | brown solid | 100 | 100 |
| 22 | [structure] | 546, 544 | white solid | 50 | 13 |
| 23 | [structure] | 572, 572 | tan solid | 25 | 0 |
| 24 | [structure] | 546, 544 | tan solid | 100 | 100 |
| 25 | [structure] | 546, 544 | orange solid | 100 | 100 |
| 26 | [structure] | 560, 558 | off white solid | 50 | 100 |
| 27 | [structure] | 507, 505 | tan solid | 100 | 100 |

TABLE 1-continued
| | | | | | |
|---|---|---|---|---|---|
| 28 | 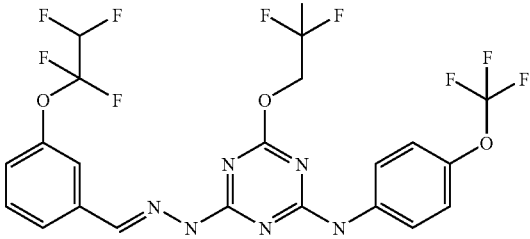 | 589, 587 | amber glass | 100 | 100 |
| 29 | 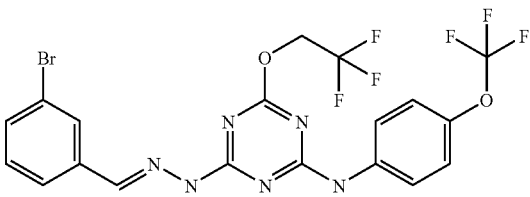 | (553, 551), (551, 549) | tan solid | 100 | 100 |
| 30 | 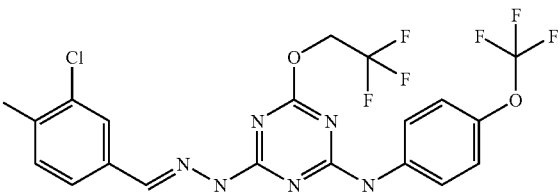 | 541, 538 | amber glass | 100 | 100 |
| 31 | 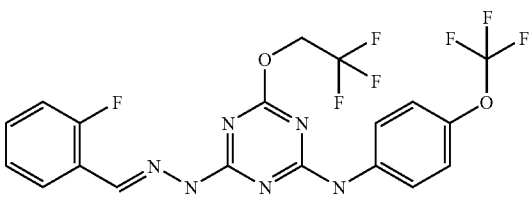 | 491, 489 | amber glass | 100 | 100 |
| 32 | 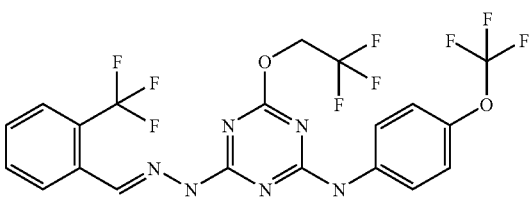 | 541, 539 | amber glass | 100 | 100 |
| 33 | 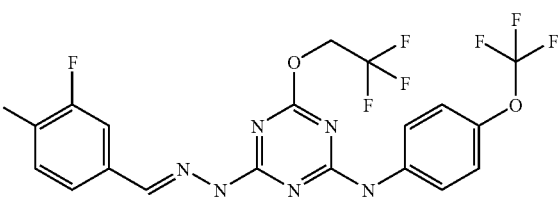 | 525, 523 | am,ber glass | 100 | 100 |
| 34 | 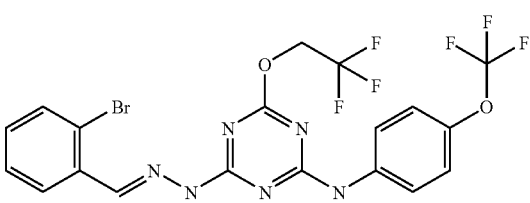 | 551, 555 | amber glass | 100 | 100 |

TABLE 1-continued
| | | | | | | |
|---|---|---|---|---|---|---|
| 35 | 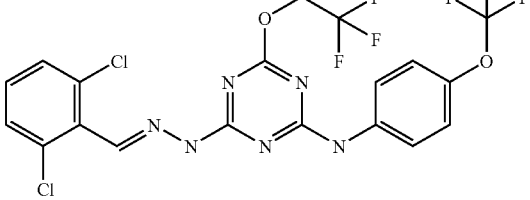 | 541, 538 | amber glass | 100 | 100 |
| 36 | 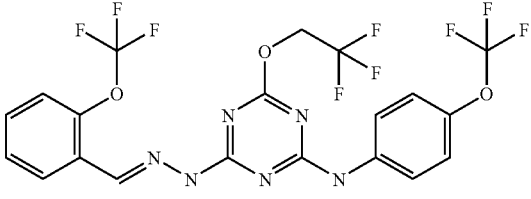 | 557, 555 | amber glass | 100 | 100 |
| 37 | 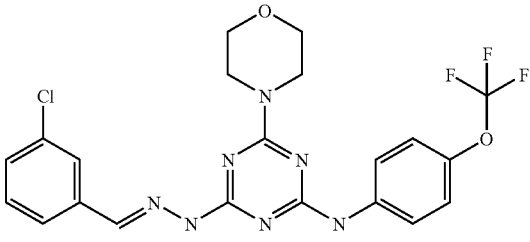 | 494, 492 | white solid | 75 | 100 |
| 38 | 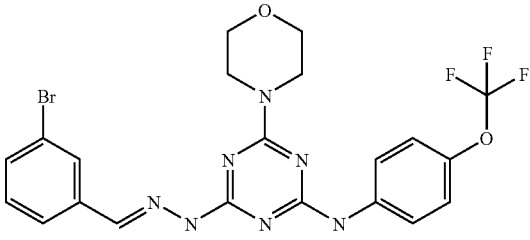 | 540, 538 | white solid | 0 | 100 |
| 39 | 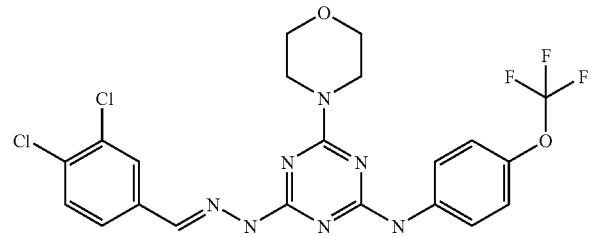 | 528, 526 | white solid | 88 | 100 |
| 40 | 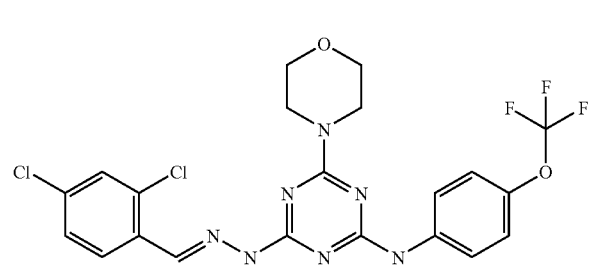 | 528, 526 | white solid | 25 | 0 |

TABLE 1-continued
| | | | | | |
|---|---|---|---|---|---|
| 41 | 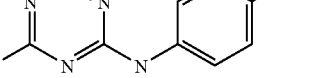 | 528, 526 | white solid | 13 | 0 |
| 42 |  | 512, 510 | white solid | 88 | 100 |
| 43 | 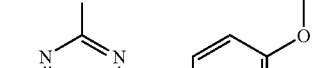 | 540, 538 | white solid | 13 | 0 |
| 44 | 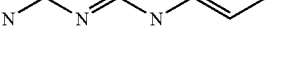 | 528, 526 | white solid | 13 | 0 |
| 45 |  | 544, 542 | white solid | 38 | 13 |
| 46 | 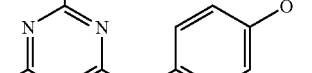 | 574, 572 | white solid | 100 | 100 |

TABLE 1-continued

| 47 | [structure] | 576, 574 | white solid | 100 | 75 |
| 48 | [structure] | 620, 618 | white solid | 13 | 0 |
| 49 | [structure] | 606, 604 | white solid | 100 | 100 |
| 50 | [structure] | 571, 569 | yellow glass | 100 | 100 |
| 51 | [structure] | 633, 631 | white solid | 100 | 100 |
| 52 | [structure] | 578, 576 | white solid | 100 | 100 |

TABLE 1-continued

| | | | | | |
|---|---|---|---|---|---|
| 53 | (structure) | 578, 576 | white solid | 100 | 100 |
| 54 | (structure) | 546, 544 | white solid | 100 | 100 |
| 55 | (structure) | 615, 613 | white solid | 100 | 63 |
| 56 | (structure) | 615, 613 | white solid | 100 | 63 |

TABLE 1-continued

| | | | | | |
|---|---|---|---|---|---|
| 57 | [structure] | 582, 580 | white solid | 100 | 100 |
| 58 | [structure] | 488, 486 | tan solid | 100 | 100 |
| 59 | [structure] | 566, 564 | yellow solid | 100 | 100 |
| 60 | [structure] | 601, 599 | clear gum | 100 | 100 |

TABLE 1-continued

| Cmpd# | Molecular Structure | Melting Point (° C.) | Phys. App | AVG LAPHEG 50 | AVG HELIZE 50 |
|---|---|---|---|---|---|
| 61 | 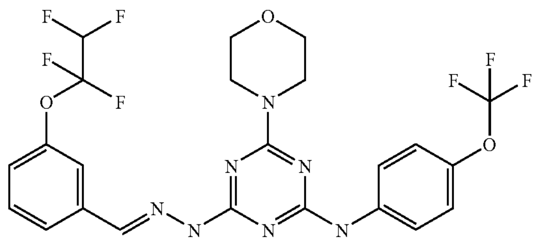 | 175.176 | white solid | 100 | 100 |
| 62 | 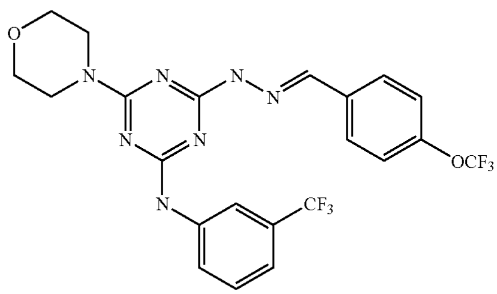 | 215-216 | white solid | 100 | 100 |
| 63 | 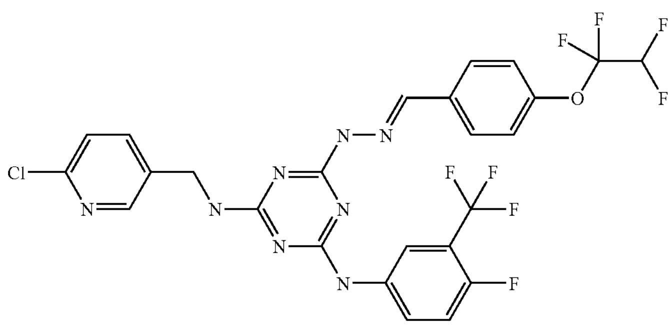 | 46-46 | clear yellow glass | 100 | 100 |
| 64 | 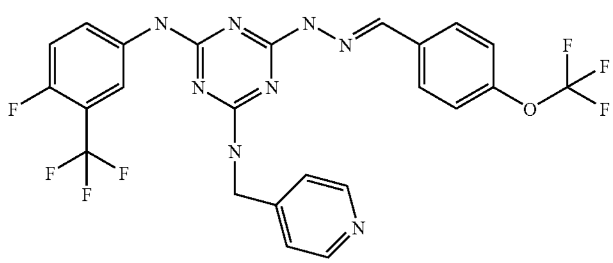 | 118-125 | light orange solid | 100 | 100 |
| 65 | 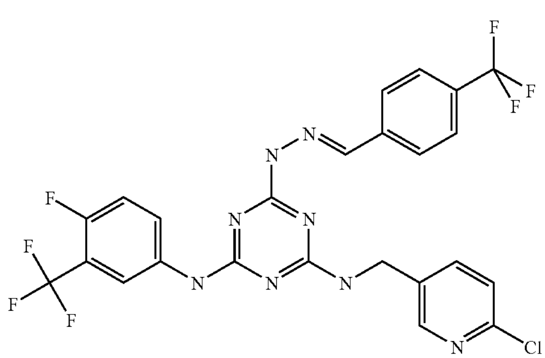 | 103-105 | tan solid | 100 | 100 |

TABLE 1-continued

| | | | | | |
|---|---|---|---|---|---|
| 66 | (structure) | 105-107 | white solid | 100 | 100 |
| 67 | (structure) | 176-178 | white solid | 100 | 100 |
| 68 | (structure) | 213-214 | off white solid | 100 | 100 |
| 69 | (structure) | 115-117 | off white solid | 100 | 100 |
| 70 | (structure) | 130-132 | off white solid | 100 | 100 |

TABLE 1-continued

| | | | | | |
|---|---|---|---|---|---|
| 71 | (structure) | 191-193 | white solid | 100 | 100 |
| 72 | (structure) | 182-183 | white solid | 0 | 25 |
| 73 | (structure) | 106-108 | white solid | 100 | 100 |
| 74 | (structure) | 108-110 | off white solid | 100 | 100 |
| 75 | (structure) | 215-216 | off white solid | 100 | 100 |

TABLE 1-continued

| # | Structure | mp (°C) | Appearance | | |
|---|---|---|---|---|---|
| 76 | (structure) | 85-87 | off white solid | 100 | 100 |
| 77 | (structure) | 93-95 | white solid | 100 | 100 |
| 78 | (structure) | 218-220 | white solid | 13 | 88 |
| 79 | (structure) | 171-173 | yellow solid | 13 | 100 |
| 80 | (structure) | 91-95 | white solid | 100 | 100 |

TABLE 1-continued
| | | | | | |
|---|---|---|---|---|---|
| 81 | 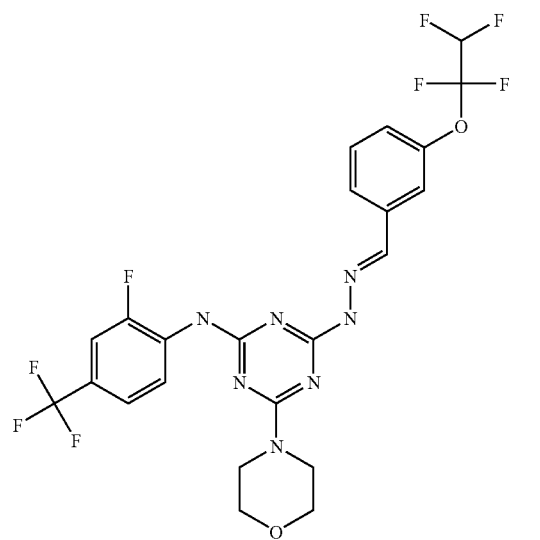 | 143-147 | white solid | 100 | 100 |
| 82 | 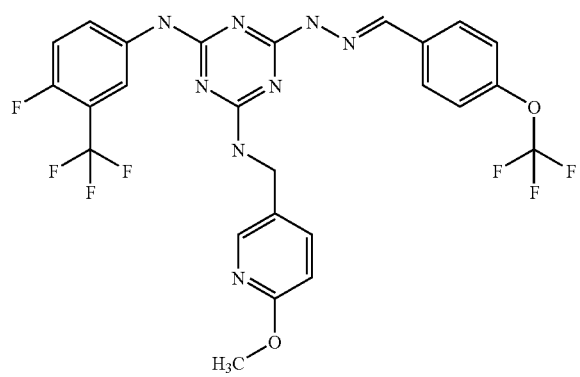 | 86-87 | white solid | 100 | 100 |
| 83 | 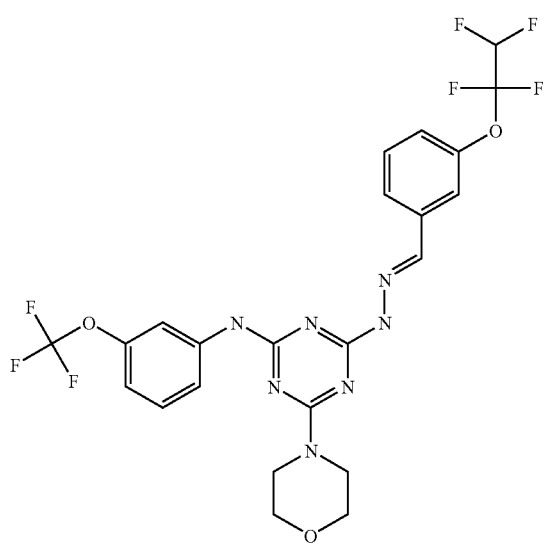 | 82-85 | white solid | 100 | 100 |

TABLE 1-continued

| # | Structure | mp (°C) | Appearance | | |
|---|---|---|---|---|---|
| 84 | (structure) | 229-230 | white solid | 25 | 75 |
| 85 | (structure) | 103-105 | white solid | 100 | 100 |
| 86 | (structure) | 99-101 | white solid | 100 | 100 |
| 87 | (structure) | 130-132 | off white solid | 100 | 100 |
| 88 | (structure) | 109-111 | white solid | 100 | 100 |

TABLE 1-continued

| # | Structure | mp (°C) | Appearance | | |
|---|---|---|---|---|---|
| 89 | (structure) | 214-215 | white solid | 100 | 100 |
| 93 | (structure) | 108-110 | light brown solid | 100 | 100 |
| 94 | (structure) | 123-125 | off white solid | 100 | 100 |
| 95 | (structure) | 105-107 | light yellow aolid | 75 | 38 |

TABLE 1-continued

| Cmpd# | Molecular Structure | Melting Point (° C.) | Appearance | AVG LAPHEG 50 | AVG HELIZE 50 |
|---|---|---|---|---|---|
| 96 | 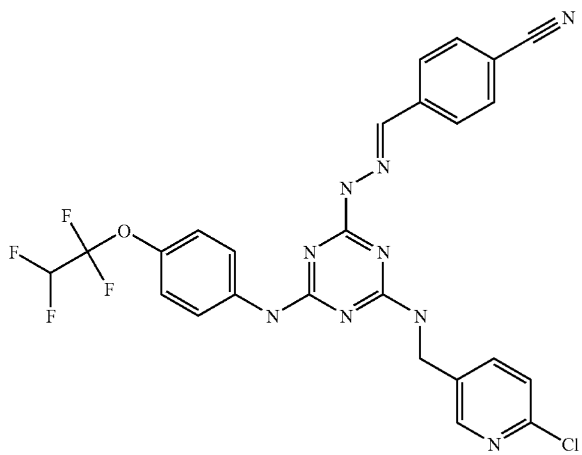 | 178-180 | off white solid | 100 | 100 |
| 97 | 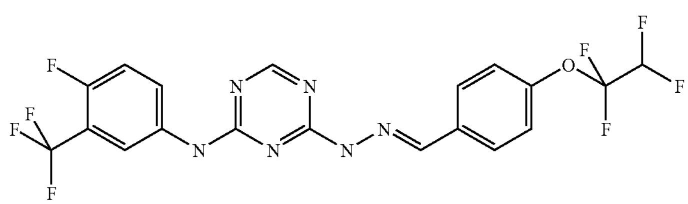 | 179-180 | white solid | 100 | 100 |
| 98 | 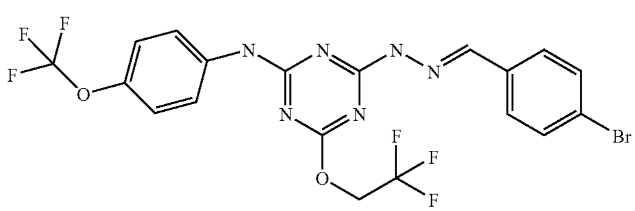 | 185-186 | white solid | 100 | 100 |
| 99 | 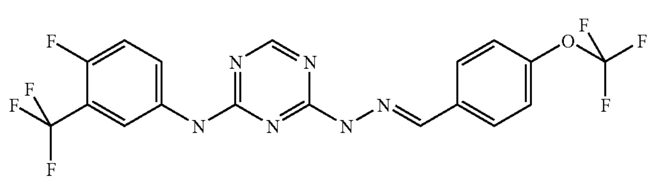 | 185-186 | white solid | 100 | 100 |
| 100 | 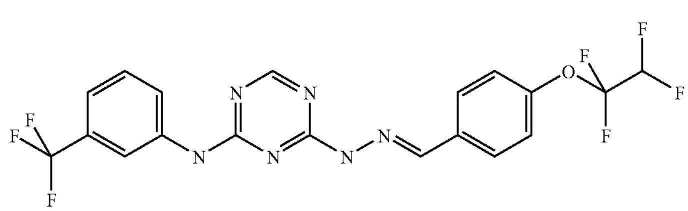 | 207-208 | white solid | 100 | 100 |
| 101 | 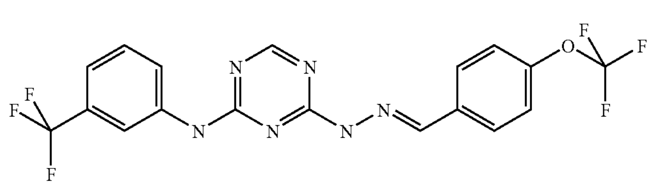 | 200-201 | white solid | 100 | 100 |

| | | | | | |
|---|---|---|---|---|---|
| 102 | 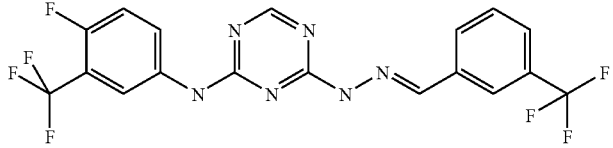 | 105-108 | off white solid | 100 | 100 |
| 103 | 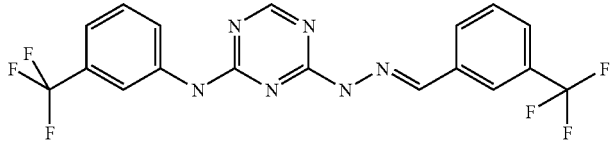 | 169-170 | white solid | 38 | 100 |
| 104 | 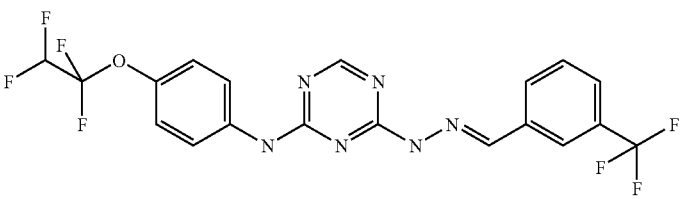 | 237-238 | white solid | 50 | 88 |

Insecticide Utility

The compounds of the invention are useful for the control of invertebrates including insects. Therefore, the present invention also is directed to a method for inhibiting an insect which comprises applying an insect-inhibiting amount of a compound of formula (I) to a locus of the insect, to the area to be protected, or directly on the insect to be controlled. The compounds of the invention may also be used to control other invertebrate pests such as mites and nematodes.

The "locus" of insects or other pests is a term used herein to refer to the environment in which the insects or other pests live or where their eggs are present, including the air surrounding them, the food they eat, or objects which they contact. For example, insects which eat, damage or contact edible, commodity, ornamental, turf or pasture plants can be controlled by applying the active compounds to the seed of the plant before planting, to the seedling, or cutting which is planted, the leaves, stems, fruits, grain, and/or roots, or to the soil or other growth medium before or after the crop is planted. Protection of these plants against virus, fungus or bacterium diseases may also be achieved indirectly through controlling sap-feeding pests such as whitefly, plant hopper, aphid and spider mite. Such plants include those which are bred through conventional approaches and which are genetically modified using modern biotechnology to gain insect-resistant, herbicide-resistant, nutrition-enhancement, and/or any other beneficial traits.

It is contemplated that the compounds might also be useful to protect textiles, paper, stored grain, seeds and other foodstuffs, houses and other buildings which may be occupied by humans and/or companion, farm, ranch, zoo, or other animals, by applying an active compound to or near such objects. Domesticated animals, buildings or human beings might be protected with the compounds by controlling invertebrate and/or nematode pests that are parasitic or are capable of transmitting infectious diseases. Such pests include, for example, chiggers, ticks, lice, mosquitoes, flies, fleas and heartworms. Nonagronomic applications also include invertebrate pest control in forests, in yards, along road sides and railroad right of way.

The term "inhibiting an insect" refers to a decrease in the numbers of living insects, or a decrease in the number of viable insect eggs. The extent of reduction accomplished by a compound depends, of course, upon the application rate of the compound, the particular compound used, and the target insect species. At least an inactivating amount should be used. The term "insect-inactivating amount" is used to describe the amount, which is sufficient to cause a measurable reduction in the treated insect population. Generally an amount in the range from about 1 to about 1000 ppm by weight active compound is used. For example, insects or other pests which can be inhibited include, but are not limited to:

Lepidoptera—*Heliothis* spp., *Helicoverpa* spp., *Spodoptera* spp., *Mythimna unipuncta*, *Agrotis ipsilon*, *Earias* spp., *Euxoa auxiliaris*, *Trichoplusia ni*, *Anticarsia gemmatalis*, *Rachiplusia nu*, *Plutella xylostella*, *Chilo* spp., *Scirpophaga incertulas*, *Sesamia inferens*, *Cnaphalocrocis medinalis*, *Ostrinia nubilalis*, *Cydia pomonella*, *Carposina niponensis*, *Adoxophyes orana*, *Archips argyrospilus*, *Pandemis heparana*, *Epinotia aporema*, *Eupoecilia ambiguella*, *Lobesia botrana*, *Polychrosis viteana*, *Pectinophora gossypiella*, *Pieris rapae*, *Phyllonorycter* spp., *Leucoptera malifoliella*, *Phyllocnisitis citrella*

Coleoptera—*Diabrotica* spp., *Leptinotarsa decemlineata*, *Oulema oryzae*, *Anthonomus grandis*, *Lissorhoptrus oryzophilus*, *Agriotes* spp., *Melanotus communis*, *Popillia japonica*, *Cyclocephala* spp., *Tribolium* spp.

Homoptera—*Aphis* spp., *Myzus persicae*, *Rhopalosiphum* spp., *Dysaphis plantaginea*, *Toxoptera* spp., *Macrosiphum euphorbiae*, *Aulacorthum solani*, *Sitobion avenae*, *Metopolophium dirhodum*, *Schizaphis graminum*, *Brachycolus noxius*, *Nephotettix* spp., *Nilaparvata lugens*, *Sogatella furcifera*, *Laodelphax striatellus*, *Bemisia tabaci*, *Trialeurodes vaporariorum*, *Aleurodes proletella*, *Aleurothrixus floccosus*, *Quadraspidiotus perniciosus*, *Unaspis yanonensis*, *Ceroplastes rubens*, *Aonidiella aurantii*

Hemiptera—*Lygus* spp., *Eurygaster maura*, *Nezara viridula*, *Piezodorus guildingi*, *Leptocorisa varicornis*, *Cimex lectularius*, *Cimex hemipterus*

Thysanoptera—*Frankliniella* spp., *Thrips* spp., *Scirtothrips dorsalis*

Isoptera—*Reticulitermes flavipes*, *Coptotermes formosanus*, *Reticulitermes virginicus*, *Heterotermes aureus*, *Reticulitermes hesperus*, *Coptotermes frenchii*, *Shedorhinotermes* spp., *Reticulitermes santonensis, Reticulitermes grassei, Reticulitermes banyulensis, Reticulitermes speratus, Reticulitermes hageni, Reticulitermes tibialis, Zootermopsis* spp., *Incisitermes* spp., *Marginitermes* spp., *Macrotermes* spp., *Microcerotermes* spp., *Microtermes* spp.

Diptera—*Liriomyza* spp., *Musca domestica, Aedes* spp., *Culex* spp., *Anopheles* spp., *Fannia* spp., *Stomoxys* spp., Hymenoptera—*Iridomyrmex humilis, Solenopsis* spp., *Monomorium pharaonis, Atta* spp., *Pogonomyrmex* spp., *Camponotus* spp., *Monomorium* spp., *Tapinoma sessile, Tetramorium* spp., *Xylocapa* spp., *Vespula* spp., *Polistes* spp.

Mallophaga (chewing lice)

Anoplura (sucking lice)—*Pthirus pubis, Pediculus* spp.

Orthoptera (grasshoppers, crickets)—*Melanoplus* spp., *Locusta migratoria, Schistocerca gregaria, Gryllotalpidae* (mole crickets).

Blattoidea (cockroaches)—*Blatta orientalis, Blattella germanica, Periplaneta americana, Supella longipalpa, Periplaneta australasiae, Periplaneta brunnea, Parcoblatta pennsylvanica, Periplaneta fuliginosa, Pycnoscelus surinamensis,*

Siphonaptera—*Ctenophalides* spp., *Pulex irritans*

Acari—*Tetranychus* spp., *Panonychus* spp., *Eotetranychus carpini, Phyllocoptruta oleivora, Aculus pelekassi, Brevipalpus phoenicis, Boophilus* spp., *Dermacentor variabilis, Rhipicephalus sanguineus, Amblyomma americanum, Ixodes* spp., *Notoedres cati, Sarcoptes scabiei, Dermatophagoides* spp.

Nematoda—*Dirofilaria immitis, Meloidogyne* spp., *Heterodera* spp., *Hoplolaimus columbus, Belonolaimus* spp., *Pratylenchus* spp., *Rotylenchus reniformis, Criconemella ornata, Ditylenchus* spp., *Aphelenchoides besseyi, Hirschmanniella* spp.

Compositions

The compounds of this invention are applied in the form of compositions which are important embodiments of the invention, and which comprise a compound of this invention and a phytologically-acceptable inert carrier. Control of the pests is achieved by applying compounds of the invention in forms of sprays, topical treatment, gels, seed coatings, microcapsulations, systemic uptake, baits, eartags, boluses, foggers, fumigants aerosols, dusts and many others. The compositions are either concentrated solid or liquid formulations which are dispersed in water for application, or are dust or granular formulations which are applied without further treatment. The compositions are prepared according to procedures and formulae which are conventional in the agricultural chemical art, but which are novel and important because of the presence therein of the compounds of this invention. Some description of the formulation of the compositions will be given, however, to assure that agricultural chemists can readily prepare any desired composition.

The dispersions in which the compounds are applied are most often aqueous suspensions or emulsions prepared from concentrated formulations of the compounds. Such water-soluble, water-suspendable or emulsifiable formulations are either solids, usually known as wettable powders, or liquids usually known as emulsifiable concentrates or aqueous suspensions. Wettable powders, which may be compacted to form water dispersible granules, comprise an intimate mixture of the active compound, an inert carrier, and surfactants. The concentration of the active compound is usually from about 10% to about 90% by weight. The inert carrier is usually chosen from among the attapulgite clays, the montmorillonite clays, the diatomaceous earths, or the purified silicates. Effective surfactants, comprising from about 0.5% to about 10% of the wettable powder, are found among the sulfonated lignins, the condensed naphthalenesulfonates, the naphthalenesulfonates, the alkylbenzenesulfonates, the alkyl sulfates, and nonionic surfactants such as ethylene oxide adducts of alkyl phenols.

Emulsifiable concentrates of the compounds comprise a convenient concentration of a compound, such as from about 50 to about 500 grams per liter of liquid, equivalent to about 10% to about 50%, dissolved in an inert carrier which is either a water miscible solvent or a mixture of water-immiscible organic solvent and emulsifiers. Useful organic solvents include aromatics, especially the xylenes, and the petroleum fractions, especially the high-boiling naphthalenic and olefinic portions of petroleum such as heavy aromatic naphtha. Other organic solvents may also be used, such as the terpenic solvents including rosin derivatives, aliphatic ketones such as cyclohexanone, and complex alcohols such as 2-ethoxyethanol. Suitable emulsifiers for emulsifiable concentrates are chosen from conventional anionic and/or nonionic surfactants, such as those discussed above.

Aqueous suspensions comprise suspensions of water-insoluble compounds of this invention, dispersed in an aqueous vehicle at a concentration in the range from about 5% to about 50% by weight. Suspensions are prepared by finely grinding the compound, and vigorously mixing it into a vehicle comprised of water and surfactants chosen from the same types discussed above. Inert ingredients, such as inorganic salts and synthetic or natural gums, may also be added, to increase the density and viscosity of the aqueous vehicle. It is often most effective to grind and mix the compound at the same time by preparing the aqueous mixture, and homogenizing it in an implement such as a sand mill, ball mill, or piston-type homogenizer.

The compounds may also be applied as granular compositions, which are particularly useful for applications to the soil. Granular compositions usually contain from about 0.5% to about 10% by weight of the compound, dispersed in an inert carrier which consists entirely or in large part of clay or a similar inexpensive substance. Such compositions are usually prepared by dissolving the compound in a suitable solvent and applying it to a granular carrier which has been pre-formed to the appropriate particle size, in the range of from about 0.5 to 3 mm. Such compositions may also be formulated by making a dough or paste of the carrier and compound and crushing and drying to obtain the desired granular particle size.

Dusts containing the compounds are prepared simply by intimately mixing the compound in powdered form with a suitable dusty agricultural carrier, such as kaolin clay, ground volcanic rock, and the like. Dusts can suitably contain from about 1% to about 10% of the compound.

It is equally practical, when desirable for any reason, to apply the compound in the form of a solution in an appropriate organic solvent, usually a bland petroleum oil, such as the spray oils, which are widely used in agricultural chemistry.

Insecticides and acaricides are generally applied in the form of a dispersion of the active ingredient in a liquid carrier. It is conventional to refer to application rates in terms of the concentration of active ingredient in the carrier. The most widely used carrier is water.

The compounds of the invention can also be applied in the form of an aerosol composition. In such compositions the active compound is dissolved or dispersed in an inert carrier, which is a pressure-generating propellant mixture. The aerosol composition is packaged in a container from which the mixture is dispensed through an atomizing valve. Propellant mixtures comprise either low-boiling halocarbons, which may be mixed with organic solvents, or aqueous suspensions pressurized with inert gases or gaseous hydrocarbons.

The actual amount of compound to be applied to loci of insects and mites is not critical and can readily be determined by those skilled in the art in view of the examples above. In general, concentrations from 10 ppm to 5000 ppm by weight of compound are expected to provide good control. With many of the compounds, concentrations from 100 to 1500 ppm will suffice.

The locus to which a compound is applied can be any locus inhabited by an insect or mite, for example, vegetable crops, fruit and nut trees, grape vines, ornamental plants, domesticated animals, the interior or exterior surfaces of buildings, and the soil around buildings.

Because of the unique ability of insect eggs to resist toxicant action, repeated applications may be desirable to control newly emerged larvae, as is true of other known insecticides and acaricides.

Systemic movement of compounds of the invention in plants may be utilized to control pests on one portion of the plant by applying the compounds to a different portion of it. For example, control of foliar-feeding insects can be controlled by drip irrigation or furrow application, or by treating the seed before planting. Seed treatment can be applied to all types of seeds, including those from which plants genetically transformed to express specialized traits will germinate. Representative examples include those expressing proteins toxic to invertebrate pests, such as *Bacillus thuringiensis* or other insecticidal proteins, those expressing herbicide resistance, such as "Roundup Ready®" seed, or those with "stacked" foreign genes expressing insecticidal proteins, herbicide resistance, nutrition-enhancement and/or any other beneficial traits.

An insecticidal bait composition consisting of compounds of the present invention and attractants and/or feeding stimulants may be used to increase efficacy of the insecticides against insect pest in a device such as trap, bait station, and the like. The bait composition is usually a solid, semi-solid (including gel) or liquid bait matrix including the stimulants and one or more non-microencapsulated or microencapsulated insecticides in an amount effective to act as kill agents.

The compounds of the present invention (Formula I) are often applied in conjunction with one or more other insecticides or fungicides or herbicides to obtain control of a wider variety of pests diseases and weeds. When used in conjunction with other insecticides or fungicides or herbicides, the presently claimed compounds can be formulated with the other insecticides or fungicides or herbicide, tank mixed with the other insecticides or fungicides or herbicides, or applied sequentially with the other insecticides or fungicides or herbicides.

Some of the insecticides that can be employed beneficially in combination with the compounds of the present invention include: antibiotic insecticides such as allosamidin and thuringiensin; macrocyclic lactone insecticides such as spinosad, spinetoram, and other spinosyns including the 21-butenyl spinosyns and their derivatives; avermectin insecticides such as abamectin, doramectin, emamectin, eprinomectin, ivermectin and selamectin; milbemycin insecticides such as lepimectin, milbemectin, milbemycin oxime and moxidectin; arsenical insecticides such as calcium arsenate, copper acetoarsenite, copper arsenate, lead arsenate, potassium arsenite and sodium arsenite; biological insecticides such as *Bacillus popilliae, B. sphaericus, B. thuringiensis* subsp. *aizawai, B. thuringiensis* subsp. *kurstaki, B. thuringiensis* subsp. *tenebrionis, Beauveria bassiana, Cydia pomonella* granulosis virus, Douglas fir tussock moth NPV, gypsy moth NPV, *Helicoverpa zea* NPV, Indian meal moth granulosis virus, *Metarhizium anisopliae, Nosema locustae, Paecilomyces fumosoroseus, P. lilacinus, Photorhabdus luminescens, Spodoptera exigua* NPV, trypsin modulating oostatic factor, *Xenorhabdus nematophilus*, and *X. bovienii*, plant incorporated protectant insecticides such as Cry1Ab, Cry1Ac, Cry1F, Cry1A.105, Cry2Ab2, Cry3A, mir Cry3A, Cry3Bb1, Cry34, Cry35, and VIP3A; botanical insecticides such as anabasine, azadirachtin, d-limonene, nicotine, pyrethrins, cinerins, cinerin I, cinerin II, jasmolin I, jasmolin II, pyrethrin I, pyrethrin II, quassia, rotenone, ryania and sabadilla; carbamate insecticides such as bendiocarb and carbaryl; benzofuranyl methylcarbamate insecticides such as benfuracarb, carbofuran, carbosulfan, decarbofuran and furathiocarb; dimethylcarbamate insecticides dimitan, dimetilan, hyquincarb and pirimicarb; oxime carbamate insecticides such as alanycarb, aldicarb, aldoxycarb, butocarboxim, butoxycarboxim, methomyl, nitrilacarb, oxamyl, tazimcarb, thiocarboxime, thiodicarb and thiofanox; phenyl methylcarbamate insecticides such as allyxycarb, aminocarb, bufencarb, butacarb, carbanolate, cloethocarb, dicresyl, dioxacarb, EMPC, ethiofencarb, fenethacarb, fenobucarb, isoprocarb, methiocarb, metolcarb, mexacarbate, promacyl, promecarb, propoxur, trimethacarb, XMC and xylylcarb; dinitrophenol insecticides such as dinex, dinoprop, dinosam and DNOC; fluorine insecticides such as barium hexafluorosilicate, cryolite, sodium fluoride, sodium hexafluorosilicate and sulfluramid; formamidine insecticides such as amitraz, chlordimeform, formetanate and formparanate; fumigant insecticides such as acrylonitrile, carbon disulfide, carbon tetrachloride, chloroform, chloropicrin, para-dichlorobenzene, 1,2-dichloropropane, ethyl formate, ethylene dibromide, ethylene dichloride, ethylene oxide, hydrogen cyanide, iodomethane, methyl bromide, methylchloroform, methylene chloride, naphthalene, phosphine, sulfuryl fluoride and tetrachloroethane; inorganic insecticides such as borax, calcium polysulfide, copper oleate, mercurous chloride, potassium thiocyanate and sodium thiocyanate; chitin synthesis inhibitors such as bistrifluron, buprofezin, chlorfluazuron, cyromazine, diflubenzuron, flucycloxuron, flufenoxuron, hexaflumuron, lufenuron, novaluron, noviflumuron, penfluron, teflubenzuron and triflumuron; juvenile hormone mimics such as epofenonane, fenoxycarb, hydroprene, kinoprene, methoprene, pyriproxyfen and triprene; juvenile hormones such as juvenile hormone I, juvenile hormone II and juvenile hormone III; moulting hormone agonists such as chromafenozide, halofenozide, methoxyfenozide and tebufenozide; moulting hormones such as α-ecdysone and ecdysterone; moulting inhibitors such as diofenolan; precocenes such as precocene I, precocene II and precocene III; unclassified insect growth regulators such as dicyclanil; nereistoxin analogue insecticides such as bensultap, cartap, thiocyclam and thiosultap; nicotinoid insecticides such as flonicamid; nitroguanidine insecticides such as clothianidin, dinotefuran, imidacloprid and thiamethoxam; nitromethylene insecticides such as nitenpyram and nithiazine; pyridylmethylamine insecticides such as acetamiprid, imidacloprid, nitenpyram and thiacloprid; organochlorine insecticides such as bromo-DDT, camphechlor, DDT, pp'-DDT, ethyl-DDD, HCH, gamma-HCH, lindane, methoxychlor, pentachlorophenol and TDE; cyclodiene insecticides such as aldrin, bromocyclen, chlorbicyclen, chlordane, chlordecone, dieldrin, dilor, endosulfan, endrin, HEOD, heptachlor, HHDN, isobenzan, isodrin, kelevan and mirex; organophosphate insecticides such as bromfenvinfos, chlorfenvinphos, crotoxyphos, dichlorvos, dicrotophos, dimethylvinphos, fospirate, heptenophos, methocrotophos, mevinphos, monocrotophos, naled, naftalofos, phosphamidon, propaphos, TEPP and tetrachlorvinphos; organothiophosphate insecticides such as dioxabenzofos, fosmethilan and phenthoate; aliphatic organothiophosphate insecticides such as acethion, amiton, cadusafos, chlorethoxyfos, chlormephos, demephion, demephion-O, demephion-S, demeton, demeton-O, demeton-S, demeton-methyl, demeton-O-methyl, demeton-S-methyl, demeton-S-methylsulphon, disulfoton, ethion, ethoprophos, IPSP, isothioate, malathion, methacrifos, oxydemeton-methyl, oxydeprofos, oxydisulfoton, phorate, sulfotep, terbufos and thiometon; aliphatic amide organothiophosphate insecticides such as amidithion, cyanthoate, dimethoate, ethoate-methyl, formothion, mecarbam, omethoate, prothoate, sophamide and vamidothion; oxime organothiophosphate insecticides such as chlorphoxim, phoxim and phoxim-methyl; heterocyclic organothiophosphate insecticides such as azamethiphos, coumaphos, coumithoate, dioxathion, endothion, menazon, morphothion, phosalone, pyraclofos, pyridaphenthion and quinothion; benzothiopyran organothiophosphate insecticides such as dithicrofos and thicrofos; benzotriazine organothiophosphate insecticides such as azinphos-ethyl and azinphos-methyl; isoindole organothiophosphate insecticides such as dialifos and phosmet; isoxazole organothiophosphate insecticides such as isoxathion and zolaprofos; pyrazolopyrimidine organothiophosphate insecticides such as chlorprazophos and pyrazophos; pyridine organothiophosphate insecticides such as chlorpyrifos and chlorpyrifos-methyl; pyrimidine organothiophosphate insecticides such as butathiofos, diazinon, etrimfos, lirimfos, pirimiphos-ethyl, pirimiphos-methyl, primidophos, pyrimitate and tebupirimfos; quinoxaline organothiophosphate insecticides such as quinalphos and quinalphos-methyl; thiadiazole organothiophosphate insecticides such as athidathion, lythidathion, methidathion and prothidathion; triazole organothiophosphate insecticides such as isazofos and triazophos; phenyl organothiophosphate insecticides such as azothoate, bromophos, bromophos-ethyl, carbophenothion, chlorthiophos, cyanophos, cythioate, dicapthon, dichlofenthion, etaphos, famphur, fenchlorphos, fenitrothion fensulfothion, fenthion, fenthion-ethyl, heterophos, jodfenphos, mesulfenfos, parathion, parathion-methyl, phenkapton, phosnichlor, profenofos, prothiofos, sulprofos, temephos, trichlormetaphos-3 and trifenofos; phosphonate insecticides such as butonate and trichlorfon; phosphonothioate insecticides such as mecarphon; phenyl ethylphosphonothioate insecticides such as fonofos and trichloronat; phenyl phenylphosphonothioate insecticides such as cyanofenphos, EPN and leptophos; phosphoramidate insecticides such as crufomate, fenamiphos, fosthietan, mephosfolan, phosfolan and pirimetaphos; phosphoramidothioate insecticides such as acephate, isocarbophos, isofenphos, methamidophos and propetamphos; phosphorodiamide insecticides such as dimefox, mazidox, mipafox and schradan; oxadiazine insecticides such as indoxacarb; phthalimide insecticides such as dialifos, phosmet and tetramethrin; pyrazole insecticides such as acetoprole, ethiprole, fipronil, pyrafluprole, pyriprole, tebufenpyrad, tolfenpyrad and vaniliprole; pyrethroid ester insecticides such as acrinathrin, allethrin, bioallethrin, barthrin, bifenthrin, bioethanomethrin, cyclethrin, cyclopro-thrin, cyfluthrin, beta-cyfluthrin, cyhalothrin, gamma-cyhalothrin, lambda-cyhalothrin, cypermethrin, alpha-cypermethrin, beta-cypermethrin, theta-cypermethrin, zeta-cypermethrin, cyphenothrin, deltamethrin, dimefluthrin, dimethrin, empenthrin, fenfluthrin, fenpirithrin, fenpropathrin, fenvalerate, esfenvalerate, flucythrinate, fluvalinate, tau-fluvalinate, furethrin, imiprothrin, metofluthrin, permethrin, biopermethrin, transpermethrin, phenothrin, prallethrin, profluthrin, pyresmethrin, resmethrin, bioresmethrin, cismethrin, tefluthrin, terallethrin, tetramethrin, tralomethrin and transfluthrin; pyrethroid ether insecticides such as etofenprox, flufenprox, halfenprox, protrifenbute and silafluofen; pyrimidinamine insecticides such as flufenerim and pyrimidifen; pyrrole insecticides such as chlorfenapyr; tetronic acid insecticides such as spirodiclofen, spiromesifen and spirotetramat; thiourea insecticides such as diafenthiuron; urea insecticides such as flucofuron and sulcofuron; and unclassified insecticides such as AKD-3088, closantel, crotamiton, cyflumetofen, E2Y45, EXD, fenazaflor, fenazaquin, fenoxacrim, fenpyroximate, FKI-1033, flubendiamide, HGW86, hydramethylnon, IKI-2002, isoprothiolane, malonoben, metaflumizone, metoxadiazone, nifluridide, NNI-9850, NNI-0101, pymetrozine, pyridaben, pyridalyl, Qcide, rafoxanide, rynaxypyr, SYJ-159, triarathene and triazamate and any combinations thereof.

Some of the fungicides that can be employed beneficially in combination with the compounds of the present invention include: 2-(thiocyanatomethylthio)-benzothiazole, 2-phenylphenol, 8-hydroxyquinoline sulfate, Ampelomyces, quisqualis, azaconazole, azoxystrobin, *Bacillus subtilis*, benalaxyl, benomyl, benthiavalicarb-isopropyl, benzylaminobenzene-sulfonate (BABS) salt, bicarbonates, biphenyl, bismerthiazol, bitertanol, blasticidin-S, borax, Bordeaux mixture, boscalid, bromuconazole, bupirimate, calcium polysulfide, captafol, captan, carbendazim, carboxin, carpropamid, carvone, chloroneb, chlorothalonil, chlozolinate, Coniothyrium minitans, copper hydroxide, copper octanoate, copper oxychloride, copper sulfate, copper sulfate (tribasic), cuprous oxide, cyazofamid, cyflufenamid, cymoxanil, cyproconazole, cyprodinil, dazomet, debacarb, diammonium ethylenebis-(dithiocarbamate), dichlofluanid, dichlorophen, diclocymet, diclomezine, dichloran, diethofencarb, difenoconazole, difenzoquat ion, diflumetorim, dimethomorph, dimoxystrobin, diniconazole, diniconazole-M, dinobuton, dinocap, diphenylamine, dithianon, dodemorph, dodemorph acetate, dodine, dodine free base, edifenphos, epoxiconazole, ethaboxam, ethoxyquin, etridiazole, famoxadone, fenamidone, fenarimol, fenbuconazole, fenfuram, fenhexamid, fenoxanil, fenpiclonil, fenpropidin, fenpropimorph, fentin, fentin acetate, fentin hydroxide, ferbam, ferimzone, fluazinam, fludioxonil, flumorph, fluopicolide, fluoroimide, fluoxastrobin, fluquinconazole, flusilazole, flusulfamide, flutolanil, flutriafol, folpet, formaldehyde, fosetyl, fosetyl-aluminum, fuberidazole, furalaxyl, furametpyr, guazatine, guazatine acetates, GY-81, hexachlorobenzene, hexaconazole, hymexazol, imazalil, imazalil sulfate, imibenconazole, iminoctadine, iminoctadine triacetate, iminoctadine tris(albesilate), ipconazole, iprobenfos, iprodione, iprovalicarb, isoprothiolane, kasugamycin, kasugamycin hydrochloride hydrate, kresoxim-methyl, mancopper, mancozeb, maneb, mepanipyrim, mepronil, mercuric chloride, mercuric oxide, mercurous chloride, metalaxyl, mefenoxam, metalaxyl-M, metam, metam-ammonium, metam-potassium, metam-sodium, metconazole, methasulfocarb, methyl iodide, methyl isothiocyanate, metiram, metominostrobin, metrafenone, mildiomycin, myclobutanil, nabam, nitrothal-isopropyl, nuarimol, octhilinone, ofurace, oleic acid (fatty acids), orysastrobin, oxadixyl, oxine-copper, oxpoconazole fumarate, oxycarboxin, pefurazoate, penconazole, pencycuron, pentachlorophenol, pentachlorophenyl laurate, penthiopyrad, phenylmercury acetate, phosphonic acid, phthalide, picoxystrobin, polyoxin B, polyoxins, polyoxorim, potassium bicarbonate, potassium hydroxyquinoline sulfate, probenazole, prochloraz, procymidone, propamocarb, propamocarb hydrochloride, propiconazole, propineb, proquinazid, prothioconazole, pyraclostrobin, pyrazophos, pyributicarb, pyrifenox, pyrimethanil, pyroquilon, quinoclamine, quinoxyfen, quintozene, Reynoutria sachalinensis extract, silthiofam, simeconazole, sodium 2-phenylphenoxide, sodium bicarbonate, sodium pentachlorophenoxide, spiroxamine, sulfur, SYP-Z071, tar oils, tebuconazole, tecnazene, tetraconazole, thiabendazole, thifluzamide, thiophanate-methyl, thiram, tiadinil, tolclofos-methyl, tolylfluanid, triadimefon, triadimenol, triazoxide, tricyclazole, tridemorph, trifloxystrobin, triflumizole, triforine, triticonazole, validamycin, vinclozolin, zineb, ziram, zoxamide, *Candida oleophila, Fusarium oxysporum, Gliocladium* spp., *Phlebiopsis gigantean, Streptomyces griseoviridis, Trichoderma* spp., (RS)—N-(3,5-dichlorophenyl)-2-(methoxymethyl)-succinimide, 1,2-dichloropropane, 1,3-dichloro-1,1,3,3-tetrafluoroacetone hydrate, 1-chloro-2,4-dinitronaphthalene, 1-chloro-2-nitropropane, 2-(2-heptadecyl-2-imidazolin-1-yl)ethanol, 2,3-dihydro-5-phenyl-1,4-dithi-ine 1,1,4,4-tetraoxide, 2-methoxyethylmercury acetate, 2-methoxyethylmercury chloride, 2-methoxyethylmercury silicate, 3-(4-chlorophenyl)-5-methylrhodanine, 4-(2-nitroprop-1-enyl)phenyl thiocyanateme: ampropylfos, anilazine, azithiram, barium polysulfide, Bayer 32394, benodanil, benquinox, bentaluron, benzamacril; benzamacril-isobutyl, benzamorf, binapacryl, bis(methylmercury) sulfate, bis(tributyltin) oxide, buthiobate, cadmium calcium copper zinc chromate sulfate, carbamorph, CECA, chlobenthiazone, chloraniformethan, chlorfenazole, chlorquinox, climbazole, copper bis(3-phenylsalicylate), copper zinc chromate, cufraneb, cupric hydrazinium sulfate, cuprobam, cyclafuramid, cypendazole, cyprofuram, decafentin, dichlone, dichlozoline, diclobutrazol, dimethirimol, dinocton, dinosulfon, dinoterbon, dipyrithione, ditalimfos, dodicin, drazoxolon, EBP, ESBP, etaconazole, etem, ethirim, fenaminosulf, fenapanil, fenitropan, fluotrimazole, furcarbanil, furconazole, furconazole-cis, furmecyclox, furophanate, glyodine, griseofulvin, halacrinate, Hercules 3944, hexylthiofos, ICIA0858, isopamphos, isovaledione, mebenil, mecarbinzid, metazoxolon, methfuroxam, methylmercury dicyandiamide, metsulfovax, milneb, mucochloric anhydride, myclozolin, N-3,5-dichlorophenyl-succinimide, N-3-nitrophenylitaconimide, natamycin, N-ethylmercurio-4-toluenesulfonanilide, nickel bis(dimethyldithiocarbamate), OCH, phenylmercury dimethyldithiocarbamate, phenylmercury nitrate, phosdiphen, prothiocarb; prothiocarb hydrochloride, pyracarbolid, pyridinitril, pyroxychlor, pyroxyfur, quinacetol; quinacetol sulfate, quinazamid, quinconazole, rabenzazole, salicylanilide, SSF-109, sultropen, tecoram, thiadifluor, thicyofen, thiochlorfenphim, thiophanate, thioquinox, tioxymid, triamiphos, triarimol, triazbutil, trichlamide, urbacid, XRD-563, and zarilamid, and any combinations thereof.

Some of the herbicides that can be employed in conjunction with the compounds of the present invention include: amide herbicides such as allidochlor, beflubutamid, benzadox, benzipram, bromobutide, cafenstrole, CDEA, chlorthiamid, cyprazole, dimethenamid, dimethenamid-P, diphenamid, epronaz, etnipromid, fentrazamide, flupoxam, fomesafen, halosafen, isocarbamid, isoxaben, napropamide, naptalam, pethoxamid, propyzamide, quinonamid and tebutam; anilide herbicides such as chloranocryl, cisanilide, clomeprop, cypromid, diflufenican, etobenzanid, fenasulam, flufenacet, flufenican, mefenacet, mefluidide, metamifop, monalide, naproanilide, pentanochlor, picolinafen and propanil; arylalanine herbicides such as benzoylprop, flamprop and flamprop-M; chloroacetanilide herbicides such as acetochlor, alachlor, butachlor, butenachlor, delachlor, diethatyl, dimethachlor, metazachlor, metolachlor, S-metolachlor, pretilachlor, propachlor, propisochlor, prynachlor, terbuchlor, thenylchlor and xylachlor; sulfonanilide herbicides such as benzofluor, perfluidone, pyrimisulfan and profluazol; sulfonamide herbicides such as asulam, carbasulam, fenasulam and oryzalin; antibiotic herbicides such as bilanafos; benzoic acid herbicides such as chloramben, dicamba, 2,3,6-TBA and tricamba; pyrimidinyloxybenzoic acid herbicides such as bispyribac and pyriminobac; pyrimidinylthiobenzoic acid herbicides such as pyrithiobac; phthalic acid herbicides such as chlorthal; picolinic acid herbicides such as aminopyralid, clopyralid and picloram; quinolinecarboxylic acid herbicides such as quinclorac and quinmerac; arsenical herbicides such as cacodylic acid, CMA, DSMA, hexaflurate, MAA, MAMA, MSMA, potassium arsenite and sodium arsenite; benzoylcyclohexanedione herbicides such as mesotrione, sulcotrione, tefuryltrione and tembotrione; benzofuranyl alkylsulfonate herbicides such as benfuresate and ethofumesate; carbamate herbicides such as asulam, carboxazole chlorprocarb, dichlormate, fenasulam, karbutilate and terbucarb; carbanilate herbicides such as barban, BCPC, carbasulam, carbetamide, CEPC, chlorbufam, chlorpropham, CPPC, desmedipham, phenisopham, phenmedipham, phenmedipham-ethyl, propham and swep; cyclohexene oxime herbicides such as alloxydim, butroxydim, clethodim, cloproxydim, cycloxydim, profoxydim, sethoxydim, tepraloxydim and tralkoxydim; cyclopropylisoxazole herbicides such as isoxachlortole and isoxaflutole; dicarboximide herbicides such as benzfendizone, cinidon-ethyl, flumezin, flumiclorac, flumioxazin and flumipropyn; dinitroaniline herbicides such as benfluralin, butralin, dinitramine, ethalfluralin, fluchloralin, isopropalin, methalpropalin, nitralin, oryzalin, pendimethalin, prodiamine, profluralin and trifluralin; dinitrophenol herbicides such as dinofenate, dinoprop, dinosam, dinoseb, dinoterb, DNOC, etinofen and medinoterb; diphenyl ether herbicides such as ethoxyfen; nitrophenyl ether herbicides such as acifluorfen, aclonifen, bifenox, chlomethoxyfen, chlomitrofen, etnipromid, fluorodifen, fluoroglycofen, fluoronitrofen, fomesafen, furyloxyfen, halosafen, lactofen, nitrofen, nitrofluorfen and oxyfluorfen; dithiocarbamate herbicides such as dazomet and metam; halogenated aliphatic herbicides such as alorac, chloropon, dalapon, flupropanate, hexachloroacetone, iodomethane, methyl bromide, monochloroacetic acid, SMA and TCA; imidazolinone herbicides such as imazamethabenz, imazamox, imazapic, imazapyr, imazaquin and imazethapyr; inorganic herbicides such as ammonium sulfamate, borax, calcium chlorate, copper sulfate, ferrous sulfate, potassium azide, potassium cyanate, sodium azide, sodium chlorate and sulfuric acid; nitrile herbicides such as bromobonil, bromoxynil, chloroxynil, dichlobenil, iodobonil, ioxynil and pyraclonil; organophosphorus herbicides such as amiprofos-methyl, anilofos, bensulide, bilanafos, butamifos, 2,4-DEP, DMPA, EBEP, fosamine, glufosinate, glyphosate and piperophos; phenoxy herbicides such as bromofenoxim, clomeprop, 2,4-DEB, 2,4-DEP, difenopenten, disul, erbon, etnipromid, fenteracol and trifopsime; phenoxyacetic herbicides such as 4-CPA, 2,4-D, 3,4-DA, MCPA, MCPA-thioethyl and 2,4,5-T; phenoxybutyric herbicides such as 4-CPB, 2,4-DB, 3,4-DB, MCPB and 2,4,5-TB; phenoxypropionic herbicides such as cloprop, 4-CPP, dichlorprop, dichlorprop-P, 3,4-DP, fenoprop, mecoprop and mecoprop-P; aryloxyphenoxypropionic herbicides such as chlorazifop, clodinafop, clofop, cyhalofop, diclofop, fenoxaprop, fenoxaprop-P, fenthiaprop, fluazifop, fluazifop-P, haloxyfop, haloxyfop-P, isoxapyrifop, metamifop, propaquizafop, quizalofop, quizalofop-P and trifop; phenylenediamine herbicides such as dinitramine and prodiamine; pyrazolyl herbicides such as benzofenap, pyrazolynate, pyrasulfotole, pyrazoxyfen, pyroxasulfone and topramezone; pyrazolylphenyl herbicides such as fluazolate and pyraflufen; pyridazine herbicides such as credazine, pyridafol and pyridate; pyridazinone herbicides such as brompyrazon, chloridazon, dimidazon, flufenpyr, metflurazon, norflurazon, oxapyrazon and pydanon; pyridine herbicides such as aminopyralid, cliodinate, clopyralid, dithiopyr, fluroxypyr, haloxydine, picloram, picolinafen, pyriclor, thiazopyr and triclopyr; pyrimidinediamine herbicides such as iprymidam and tioclorim; quaternary ammonium herbicides such as cyperquat, diethamquat, difenzoquat, diquat, morfamquat and paraquat; thiocarbamate herbicides such as butylate, cycloate, di-allate, EPTC, esprocarb, ethiolate, isopolinate, methiobencarb, molinate, orbencarb, pebulate, prosulfocarb, pyributicarb, sulfallate, thiobencarb, tiocarbazil, tri-allate and vernolate; thiocarbonate herbicides such as dimexano, EXD and proxan; thiourea herbicides such as methiuron; triazine herbicides such as dipropetryn, triaziflam and trihydroxytriazine; chlorotriazine herbicides such as atrazine, chlorazine, cyanazine, cyprazine, eglinazine, ipazine, mesoprazine, procyazine, proglinazine, propazine, sebuthylazine, simazine, terbuthylazine and trietazine; methoxytriazine herbicides such as atraton, methometon, prometon, secbumeton, simeton and terbumeton; methylthiotriazine herbicides such as ametryn, aziprotryne, cyanatryn, desmetryn, dimethametryn, methoprotryne, prometryn, simetryn and terbutryn; triazinone herbicides such as ametridione, amibuzin, hexazinone, isomethiozin, metamitron and metribuzin; triazole herbicides such as amitrole, cafenstrole, epronaz and flupoxam; triazolone herbicides such as amicarbazone, bencarbazone, carfentrazone, flucarbazone, propoxycarbazone, sulfentrazone and thiencarbazone-methyl; triazolopyrimidine herbicides such as cloransulam, diclosulam, florasulam, flumetsulam, metosulam, penoxsulam and pyroxsulam; uracil herbicides such as butafenacil, bromacil, flupropacil, isocil, lenacil and terbacil; 3-phenyluracils; urea herbicides such as benzthiazuron, cumyluron, cycluron, dichloralurea, diflufenzopyr, isonoruron, isouron, methabenzthiazuron, monisouron and noruron; phenylurea herbicides such as anisuron, buturon, chlorbromuron, chloreturon, chlorotoluron, chloroxuron, daimuron, difenoxuron, dimefuron, diuron, fenuron, fluometuron, fluothiuron, isoproturon, linuron, methiuron, methyldymron, metobenzuron, metobromuron, metoxuron, monolinuron, monuron, neburon, parafluron, phenobenzuron, siduron, tetrafluron and thidiazuron; pyrimidinylsulfonylurea herbicides such as amidosulfuron, azimsulfuron, bensulfuron, chlorimuron, cyclosulfamuron, ethoxysulfuron, flazasulfuron, flucetosulfuron, flupyrsulfuron, foramsulfuron, halosulfuron, imazosulfuron, mesosulfuron, nicosulfuron, orthosulfamuron, oxasulfuron, primisulfuron, pyrazosulfuron, rimsulfuron, sulfometuron, sulfosulfuron and trifloxysulfuron; triazinylsulfonylurea herbicides such as chlorsulfuron, cinosulfuron, ethametsulfuron, iodosulfuron, metsulfuron, prosulfuron, thifensulfuron, triasulfuron, tribenuron, triflusulfuron and tritosulfuron; thiadiazolylurea herbicides such as buthiuron, ethidimuron, tebuthiuron, thiazafluron and thidiazuron; and unclassified herbicides such as acrolein, allyl alcohol, azafenidin, benazolin, bentazone, benzobicyclon, buthidazole, calcium cyanamide, cambendichlor, chlorfenac, chlorfenprop, chlorflurazole, chlorflurenol, cinmethylin, clomazone, CPMF, cresol, ortho-dichlorobenzene, dimepiperate, endothal, fluoromidine, fluridone, flurochloridone, flurtamone, fluthiacet, indanofan, methazole, methyl isothiocyanate, nipyraclofen, OCH, oxadiargyl, oxadiazon, oxaziclomefone, pentachlorophenol, pentoxazone, phenylmercury acetate, pinoxaden, prosulfalin, pyribenzoxim, pyriftalid, quinoclamine, rhodethanil, sulglycapin, thidiazimin, tridiphane, trimeturon, tripropindan and tritac.

We claim:
1. A compound of formula (I)

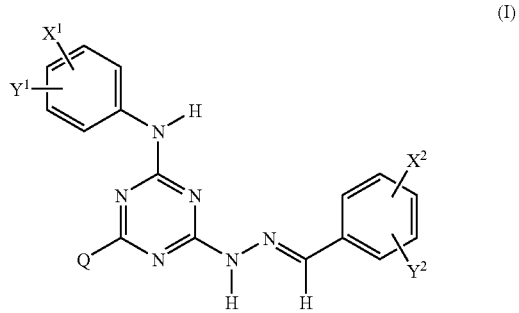

wherein
$X^1$ and $Y^1$ independently represent H, halogen, CN, $OCH_2CH=CHCl$, $C_1$-$C_6$ haloalkyl, $C_1$-$C_6$ haloalkoxy or $C_1$-$C_6$ halothioalkyl, with the proviso that at least one of $X^1$ or $Y^1$ is not H and at least one of $X^1$ and $Y^1$ is $OCF_3$ or $OCF_2CHF_2$;
$X^2$ and $Y^2$ independently represent H, halogen, CN, $OCH_2CH=CHCl$, $C_1$-$C_6$ alkoxy, $C_1$-$C_6$ haloalkyl, $C_1$-$C_6$ haloalkoxy or $C_1$-$C_6$ halothioalkyl, with the proviso that at least one of $X^2$ or $Y^2$ is not H;
Q represents H, Cl, $OR^1$ or $NR^2R^3$;
$R^1$ represents $C_1$-$C_4$ alkyl which may be unsubstituted or substituted with from one to the maximum number of chloro or fluoro substituents;
$R^2$ represents H or $C_1$-$C_4$ alkyl;
$R^3$ represents: a) $C_1$-$C_4$ alkyl which may be unsubstituted or substituted with from one to the maximum number of chloro or fluoro substituents, or with a substituent selected from the group consisting of a $C_1$-$C_4$ alkoxy, a $C_1$-$C_4$ alkylamino, a $C_1$-$C_4$ carboalkoxy, a pyridin-3-yl substituted in the 6-position of the pyridine ring with halogen, $C_1$-$C_4$ alkoxy or $C_1$-$C_4$ haloalkyl, a pyrazin-2-yl substituted in the 5-position of the pyrazine ring with ($C_1$-$C_4$)alkyl, and a mopholin-4-yl substituent; or b) $NR^2R^3$ taken together represent:

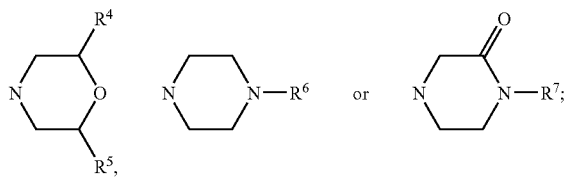

$R^4$, $R^5$ and $R^7$ independently represent H or $CH_3$; and
$R^6$ represents H, $C_1$-$C_4$ alkyl or $-C(O)R^4$;
or a phytologically acceptable acid addition salt thereof.
2. A compound according to claim 1 in which $X^1$ and $Y^1$ are meta- or para-substituents.
3. A compound according to claim 1 in which one of $X^2$ and $Y^2$ is F, Cl, Br, CN, $CF_3$, $OCF_3$ or $OCF_2CHF_2$.
4. A compound according to claim 3 in which $X^2$ and $Y^2$ are meta- or para-substituents.

5. A compound according to claim 1 in which Q is

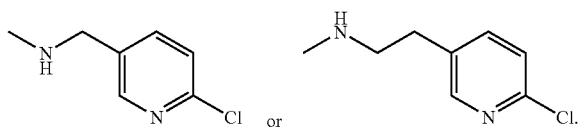

6. A composition for controlling insects which comprises a compound of claim 1 in combination with a phytologically-acceptable carrier.

7. A method of controlling insects which comprises applying to a locus where control is desired an insect-inactivating amount of a compound of claim 1.

8. A process for the preparation of a compound of formula I

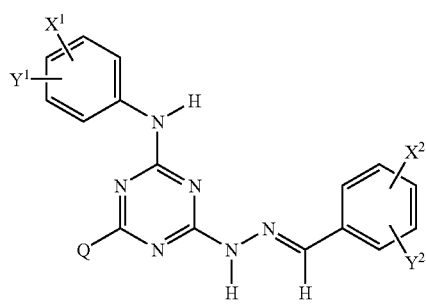
(I)

wherein
$X^1$ and $Y^1$ independently represent H, halogen, CN, $OCH_2CH=CHCl$, $C_1$-$C_6$ haloalkyl, $C_1$-$C_6$ haloalkoxy or $C_1$-$C_6$ halothioalkyl, with the proviso that at least one of $X^1$ or $Y^1$ is not H and at least one of $X^1$ and $Y^1$ is $OCF_3$ or $OCF_2CHF_2$;
$X^2$ and $Y^2$ independently represent H, halogen, CN, $OCH_2CH=CHCl$, $C_1$-$C_6$ alkoxy, $C_1$-$C_6$ haloalkyl, $C_1$-$C_6$ haloalkoxy or $C_1$-$C_6$ halothioalkyl, with the proviso that at least one of $X^2$ or $Y^2$ is not H;
Q represents H, Cl, $OR^1$ or $NR^2R^3$;
$R^1$ represents $C_1$-$C_4$ alkyl which may be unsubstituted or substituted with from one to the maximum number of chloro or fluoro substituents;
$R^2$ represents H or $C_1$-$C_4$ alkyl;
$R^3$ represents: a) $C_1$-$C_4$ alkyl which may be unsubstituted or substituted with from one to the maximum number of chloro or fluoro substituents, or with a substituent selected from the group consisting of a $C_1$-$C_4$ alkoxy, a $C_1$-$C_4$ alkylamino, a $C_1$-$C_4$ carboalkoxy, a pyridin-3-yl substituted in the 6-position of the pyridine ring with halogen, $C_1$-$C_4$ alkoxy or $C_1$-$C_4$ haloalkyl, a pyrazin-2-yl substituted in the 5-position of the pyrazine ring with $(C_1$-$C_4)$alkyl, and a mopholin-4-yl substituent; or b) $NR^2R^3$ taken together represent:

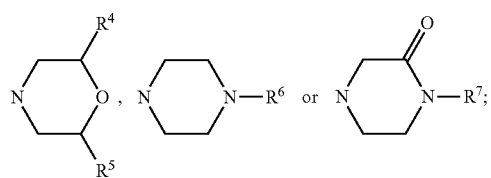

$R^4$, $R^5$ and $R^7$ independently represent H or $CH_3$; and
$R^6$ represents H, $C_1$-$C_4$ alkyl or —C(O)$R^4$;

which comprises:
(a) contacting cyanuric chloride (II)

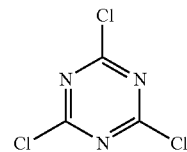
(II)

with an aniline of formula (III)

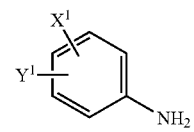
(III)

in a polar aprotic solvent in the presence of base to provide 2-anilino-4,6-dichloro-s-triazine of formula (IV) wherein $X^1$ and $Y^1$ are as previously defined

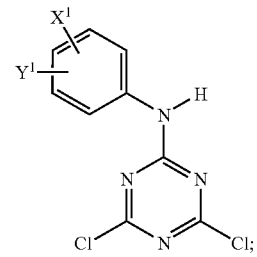
(IV)

(b) contacting the 2-anilino-4,6-dichloro-s-triazine of formula (IV) with an alcohol or an amine in a polar aprotic solvent in the presence of base to provide 2-anilino-s-triazine of formula (V) wherein $X^1$, $Y^1$ and Q are as previously defined

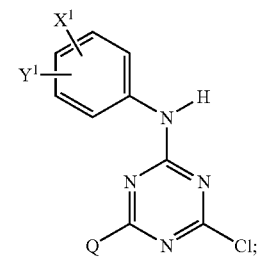
(V)

(c) contacting the 2-anilino-s-triazine of formula (V) with a hydrazine $NH_2$—$NH_2$ in a polar aprotic solvent to provide the compound of formula (VI) wherein $X^1$, $Y^1$ and Q are as previously defined

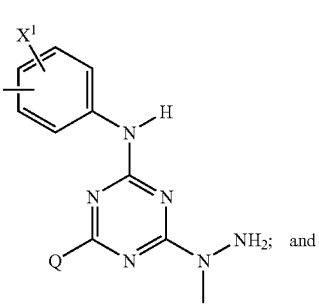
(VI)

and (d) contacting the compound of formula (VI) with a an aryl aldehyde (VII)

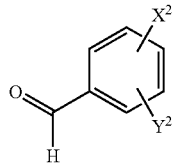

wherein $X^2$ and $Y^2$ are as previously defined;
in a polar aprotic solvent to provide the compound of formula (I).

9. A process for the preparation of a compound of formula I

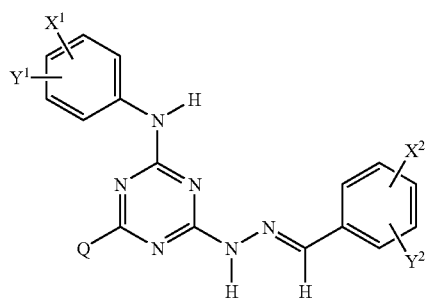

wherein
- $X^1$ and $Y^1$ independently represent H, halogen, CN, $OCH_2CH=CHCl$, $C_1$-$C_6$ haloalkyl, $C_1$-$C_6$ haloalkoxy or $C_1$-$C_6$ halothioalkyl, with the proviso that at least one of $X^1$ or $Y^1$ is not H and at least one of $X^1$ and $Y^1$ is $OCF_3$ or $OCF_2CHF_2$;
- $X^2$ and $Y^2$ independently represent H, halogen, CN, $OCH_2CH=CHCl$, $C_1$-$C_6$ alkoxy, $C_1$-$C_6$ haloalkyl, $C_1$-$C_6$ haloalkoxy or $C_1$-$C_6$ halothioalkyl, with the proviso that at least one of $X^2$ or $Y^2$ is not H;
- Q represents H, Cl, $OR^1$ or $NR^2R^3$;
- $R^1$ represents $C_1$-$C_4$ alkyl which may be unsubstituted or substituted with from one to the maximum number of chloro or fluoro substituents;
- $R^2$ represents H or $C_1$-$C_4$ alkyl;
- $R^3$ represents: a) $C_1$-$C_4$ alkyl which may be unsubstituted or substituted with from one to the maximum number of chloro or fluoro substituents, or with a substituent selected from the group consisting of a $C_1$-$C_4$ alkoxy, a $C_1$-$C_4$ alkylamino, a $C_1$-$C_4$ carboalkoxy, a pyridin-3-yl substituted in the 6-position of the pyridine ring with halogen, $C_1$-$C_4$ alkoxy or $C_1$-$C_4$ haloalkyl, a pyrazin-2-yl substituted in the 5-position of the pyrazine ring with ($C_1$-$C_4$)alkyl, and a mopholin-4-yl substituent; or b) $NR^2R^3$ taken together represent:

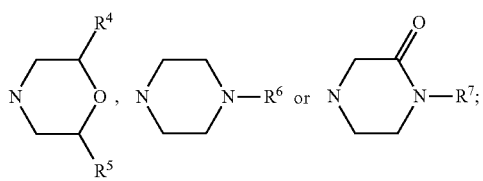

$R^4$, $R^5$ and $R^7$ independently represent H or $CH_3$; and
$R^6$ represents H, $C_1$-$C_4$ alkyl or —$C(O)R^4$;

which comprises:
a) contacting cyanuric chloride (II)

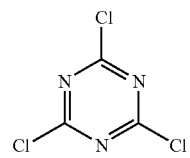

with an aniline of formula (III)

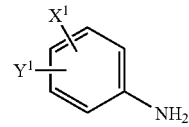

in a polar aprotic solvent in the presence of base to provide 2-anilino-4,6-dichloro-s-triazine of formula (IV) wherein $X^1$ and $Y^1$ are as previously defined

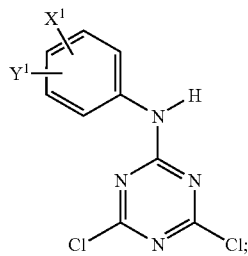

b) contacting the 2-anilino-4,6-dichloro-s-triazine of formula (IV) with an aryl hydrazone (VIII)

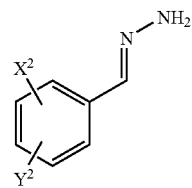

in a polar aprotic solvent in the presence of base to provide 2-anilino-s-triazine of formula (Ia) wherein $X^1$, $X^2$, $Y^1$ and $Y^2$ are as previously defined

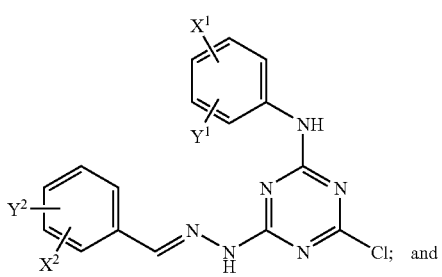

c) contacting the 2-anilino-s-triazine of formula (Ia) with an alcohol or an amine in a polar aprotic solvent in the presence of base to provide the compound of formula (I) wherein $X^1$, $X^2$, $Y^1$, $Y^2$ and Q are as previously defined.

* * * * *